US007078492B2

(12) United States Patent
Pirofski et al.

(10) Patent No.: US 7,078,492 B2
(45) Date of Patent: Jul. 18, 2006

(54) HUMAN ANTIPNEUMOCOCCAL ANTIBODIES FROM NON-HUMAN ANIMALS

(75) Inventors: Liise-anne Pirofski, New York, NY (US); Zhaojing Zhong, Bronx, NY (US); Qing Chang, Bronx, NY (US)

(73) Assignee: Abgenix, Inc., Fremont, CA (US)

( * ) Notice: Subject to any disclaimer, the term of this patent is extended or adjusted under 35 U.S.C. 154(b) by 117 days.

(21) Appl. No.: 10/714,079

(22) Filed: Nov. 14, 2003

(65) Prior Publication Data

US 2005/0014931 A1    Jan. 20, 2005

Related U.S. Application Data

(63) Continuation of application No. PCT/US02/18363, filed on May 16, 2002.

(60) Provisional application No. 60/291,492, filed on May 16, 2001.

(51) Int. Cl.
*C12P 21/08* (2006.01)
*C07K 16/00* (2006.01)
*G01N 33/53* (2006.01)

(52) U.S. Cl. .............. 530/387.3; 530/388.1; 530/388.4; 435/7.1

(58) Field of Classification Search ............ 530/387.3, 530/388.1, 388.4; 435/7.1
See application file for complete search history.

(56) References Cited

U.S. PATENT DOCUMENTS

| | | | |
|---|---|---|---|
| 4,399,216 A | 8/1983 | Axel et al. |
| 4,510,245 A | 4/1985 | Cousens et al. |
| 4,634,665 A | 1/1987 | Axel et al. |
| 4,740,461 A | 4/1988 | Kaufman |
| 4,912,040 A | 3/1990 | Kaufman et al. |
| 4,959,455 A | 9/1990 | Clark et al. |
| 4,968,615 A | 11/1990 | Koszinowski et al. |
| 5,168,062 A | 12/1992 | Stinski |
| 5,179,017 A | 1/1993 | Axel et al. |
| 5,741,957 A | 4/1998 | Deboer et al. |
| 5,750,172 A | 5/1998 | Meade et al. |
| 5,756,687 A | 5/1998 | Denman et al. |
| 5,827,690 A | 10/1998 | Meade et al. |
| 5,916,771 A | 6/1999 | Hori et al. |
| 5,939,598 A | 8/1999 | Kucherlapati et al. |
| 5,985,615 A | 11/1999 | Jakobovits et al. |
| 5,998,209 A | 12/1999 | Jokobovits et al. |
| 6,075,181 A | 6/2000 | Kucherlapati et al. |
| 6,091,001 A | 7/2000 | Jakobovits et al. |
| 6,114,598 A | 9/2000 | Kucherlapati et al. |
| 6,130,364 A | 10/2000 | Jakobovits et al. |

FOREIGN PATENT DOCUMENTS

| | | |
|---|---|---|
| EP | 0 216 846 | 1/1990 |
| EP | 0 256 055 | 8/1991 |
| EP | 0 323 997 | 4/1993 |
| EP | 0 338 841 | 3/1995 |
| WO | WO 91/10741 | 7/1991 |
| WO | WO 94/02602 | 2/1994 |
| WO | WO 96/33735 | 10/1996 |
| WO | WO 96/34096 | 10/1996 |
| WO | WO 98/16654 | 4/1998 |
| WO | WO 98/24893 | 6/1998 |
| WO | WO 98/50433 | 11/1998 |
| WO | WO 99/45031 | 9/1999 |
| WO | WO 99/53049 | 10/1999 |
| WO | WO 00/09560 | 2/2000 |
| WO | WO 00/037504 | 6/2000 |

OTHER PUBLICATIONS

Abadi, J. et al., "Human Antibodies Elicited by a Pneumococcal Vaccine Express Idiotypic Determinants Indictive of $V_H 3$ Gene Segment Usage," *J. Infect. Dis.* 178:707-716 (1998).

Bowie, J.U., et al., "A Method to Identify Protein Sequences That Fold Into a Known Three-Dimensional Structure," *Science.* 253:164-170 (1991).

Chothia, C. & Lesk, A.M., "Canonical Structures for the Hypervariable Regions of Immunoglobulins," *J. Mol. Biol.* 196:901-917 (1987).

Chothia, C., et al., "Conformations of Immunoglobulin Hypervariable Regions," *Nature* 342:877-883 (1989).

Green, L.L. & Jakobovits, A., "Regulation of B Cell development by Variable Gene Complexity in Mice Reconstituted with Human Immunoglobulin Yeast Artificial Chromosomes," *J. Exp. Med.* 188:483-495 (1998).

(Continued)

*Primary Examiner*—Mark Navarro
(74) *Attorney, Agent, or Firm*—Fish & Neave IP Group of Ropes & Gray LLP; Jane T. Gunnison; Shilpi Banerjee

(57) ABSTRACT

The invention described herein provides human antibodies produced in non-human animals that specifically bind to *Streptococcus pneumoniae* capsular polysaccharide (PPS-3). The invention further provides methods for making the antibodies in a non-human animal and for expressing the antibodies in cells including hybridomas and recombinant host cell systems. Kits and pharmaceutical compositions comprising the antibodies are also provided in addition to methods of treating, inhibitng or preventing *S. pneumoniae* infection or conditions or disorders caused by such infection by administering to a patient the pharmaceutical compositions described herein.

11 Claims, 8 Drawing Sheets

OTHER PUBLICATIONS

Green, L.L., et al., "Antigen-Specific Human Monoclonal Antibodies from Mice Engineered with Human Lg Heavy and Light Chain Yacs," *Nature Genet.* 7:13-21 (1994).

Holliger, P., et al., "'Diabodies': Small Bivalent and Bispecific Antibody Fragments," *Proc. Natl. Acad. Sci. U.S.A.* 90:6444-6448 (1993).

Johnson, G & Wu, T.T., "Kabat Database and its Applications: Future Directions," *Nucl. Acids Res.* 29:205-206 (2001).

Kaufman, R.J. and Sharp, P.A., "Amplification and Expression of Sequences Contransfected with a Modular Dihydrofolate Reductase Complementary DNA Gene," *J. Mol. Biol.* 159:601-621 (1982).

Kostelny, S.A., et al., "Formation of a Bispecific Antibody by the Use of Leucine Zippers," *J. Immunol.* 148:1547-1553 (1992).

McCormick, L.L., et al., "Bispecific Antibodies Overcome the Opsonin-Receptor Mismatch of Cystic Fibrosis In Vitro: Restoration of Neutrophil-Mediated Phagocytosis and Killing of *Pseudomonas aeruginosa*," *J Immunol.* 158:3474-82 (1997).

Mendez, M.J., et al., "Functional Transplant of Megabase Human Immunoglobulin Loci Recapitulates Human Antibody Response in Mice," *Nat. Genet.* 15, pp. 146-156 (1997).

Mukherjee, J. et al., Molecular Characterization of the Humoral Responses to *Cryptococcus neoformans* Infection and Glucuronoxylomannan- Tetanus Toxoid Conjugate Immunization, *J. Exp. Med.* 177:1105-1116 (1993).

Pirofski, L., et al., "Analysis of Human Monoclonal Antibodies Elicited by Vaccination," *Infect. Immun.* 63:3005-3014 (1995) and *Infect. Immun.* 68:1820-1826 (2000).

Russell, N.D., et al., "Production of Protective Human Antipneumococcal Antibodies by Transgenic Mice with Human Immunoglobulin Loci," *Infection Immunity* 68:1820-1826 (2000).

Russell, N.D., et al., A Tale of Two Pathogens: Human Antibody Immunity to *Crypotococcus neoformans* and *Streptococcus pneumoniae, Einstein Quart. J. Biol. Med.* 15:148-157 (1998).

Songsilvllai, S. & Lachmann, P.C., "Bispecific antibody: a tool for diagnosis and treatement of disease," *Clin. Exp. Immunol.* 79:315-321 (1990).

Thornton, J.M., et al., "Prediction of progress at last," *Nature* 354:105-106 (1991).

Traunecker, A., et al., "Bispecific single chain molecules (Janusins) target cytotoxic lymphocytes on HIV infected cells," *EMBO J.* 10:3655-3659 (1991).

Traunecker, A., et al., "Janusin: New molecular design for bispecific reagents," *Int. J. Cancer Suppl.* 7:51-52 (1992).

1F10 Heavy Chain (SEQ ID NO: 1)

5'GAGTTTGGGCTGAGCTGGCTTTTTCTTGTGGCTATTTTAAAAGGTGTCCAG
TGTGAGGTGCAGCTGTTGGAGTCTGGGGGAGGCTTGGTACAGCCTGGGGGGT
CCCTGAGACTCTCCTGTGCAGCCTCTGGATTCACCTTTAGCAGCTATGCCATG
AGCTGGGTCCGCCAGGCTCCAGGGAAGGGGCTGGAGTGGGTCTCAGCTATTA
GTGGTAGTGGTGGTAGCACATACTACGCAGACTCCGTGAAGGGCCGGTTCAC
CATCTCCAGAGACAATTCCAAGAACACGCTGTATCTGCAAATGAACAGCCTG
AGAGCCGAGGACACGGCCGTATATTACTGTGCGAAAGCCCTCCTAACTGGG
GATCGTTTGACTACTGGGGCCAGGGAACCCTGGTCACCGTCTCCTCAGGGAG
TGCATCCGCCCCAACCCTTTTCCCCCTCGTCTCCTGTGAGAATTCC3'

1F10 Light Chain (SEQ ID NO: 2)

5'GATATTGAGCTCACGCAGTCTCCACTCTCCCTGCCCGTCACCCTTGGACA
GCCGGCCTCCATCTCCTGCAGGTCTAGTCAAAGCCTCGTATACAGTGATGGA
AACACCTACTTGAATTGGTTTCAGCAGAGGCCAGGCCAATCTCCAAGGCGCC
TAATTTATAAGGTTTCTAACTGGGACTCTGGGGTCCCAGACAGATTCAGCGGC
AGTGGGTCAGGCACTGATTTCACACTGAAAATCAGCAGGGTGGAGGCTGAGG
ATGTTGGGGTTTATTACTGCATGCAAGGTACACACTGGCCTCGGACGTTCGGC
CAAGGGACCAAGGTGGAAATCAAACGAACTGTGGCTGCACCATCTGTCTTCA
TCTTCCCGCCATCTGATGAGCAGTTGAAATCTGGAACTGCCTCTGTTGTGTGC
CTGCTGAATAACTTCTATCCCAGAGAGGCCAAAGTACAGTGGAAGGTGGATA
ACGCCCTCCAATCGGGTAACTCCCAGGAGAGTGTCACAGAGCAGGACAGCA
AGGACAGCACCTACAGCCTCAGCAGCACCCTGACGCTGAGCAAAGCAGACT
ACGAGAAACACAAAGTCTACGCCTGCGAAGTCACCCATCAGGGCCTGAGCTC
GCCCGTCACAAAGAGCTTCAACAGG3'

3H1 Heavy Chain (SEQ ID NO: 3)

5'GAGTTTGGGCTGAGCTGGGTTTTCCTCGTTGCTCTTTTAAGAGGTGTCCAG
TGTCAGGTGCAACTGGTGGAGTCTGGGGGAGGCGTGGTCCAGCCTGGGAGGT
CCCTGAGACTCTCCTGTGCAGCGTCTGGATTCACCTTCAGTAGCTATGGCATG
CACTGGGTCCGCCAGGCTCCAGGCAAGGGGCTGGAGTGGGTGGCAGTTATAT
GGTATGATGGAAGTAATAAATACTATGCAGACTCCGTGAAGGGCCGATTCAC
CATCTCCAGAGACAATTCCAAGAACACGCTGTATCTGCAAATGAACAGCCTG
AGAGCCGAGGACACGGCTGTGTATTACTGTGCGAGAGATCGGGAGTGGCTGA
GGTACTACTACTACGGTATGGACGTCTGGGGCCAAGGGACCACGGTCACCGT
CTCCTCAGGGAGTGCATCCGCCCCAACCCTTTTCCCC**CTCGTCTCCTGTGAG
AATTCC**3'

FIG. 6A

3H1 Light Chain (SEQ ID NO: 4)

5'GACATTGAGCTACGCAGTCTCCATCTTCCGTGTCTGCATCTGTAGGAGAC
AGAGTCACCATCACTTGTCGGGCGAGTCAGGGTATTAGCAGCTGGTTAGCCT
GGTATCAGCAGAAACCAGGGAAAGCCCCTAAGCTCCTGATCTATGTTGCATC
CCGTTTGCAAAGTGGGGTCCCATCAAGGTTCAGCGGCAGTGGATCTGGGACA
GATTTCACTCTCACCATCAGCAGCCTGCAGCCTGAAGATTTTGCAACTTACTA
TTGTCAACAGGCTAACAGTTTCCCTCGGACGTTCGGCCAAGGGACCAAGGTG
GAAATCAAACGAACTGTGGCTGCACCATCTGTCTTCATCTTCCCGCCATCTGA
TGAGCAGTTGAAATCTGGAACTGCCTCTGTTGTGCCTGCTGAATAACTTCT
ATCCCAGAGAGGCCAAAGTACAGTGGAAGGTGGATAACGCCCTCCAATCGG
GTAACTCCCAGGAGAGTGTCACAGAGCAGGACAGCAAGGACAGCACCTACA
GCCTCAGCAGCACCCTGACGCTGAGCAAAGCAGACTACGAGAAACACAAAG
TCTACGCCTGCGAAGTCACCCATCAGGGCCTGAGCTCGCCC**GTCACAAAGAG
CTTCAACAGG**3'

1A2 Heavy Chain (SEQ ID NO: 5)

5'GAATTTGGGCTGAGCTGGATTTTCCTTGCTGCTATTTTAAAAGGTGTCCAG
TGTGAGGTGCAGCTGGTGGAGTCTGGGGGAGGCTTGGTAAAGCCTGGGGGGT
CCCTTAGACTCTCCTGTGCAGCCTCTGGATTCACTTTCAGTAACGCCTGGATG
AGCTGGGTCCGCCAGGCTCCAGGGAAGGGGCTGGAGTGGGTTGGCCGTATTA
AAAGCAAAACTGATGGTGGGACAACAGACTACGCTGCACCCGTGAAAGGCA
GATTCACCATCTCAAGAGATGATTCAAAAAACACGCTGTATCTGCAAATGAA
CAGCCTGAAAACCGAGGACACAGCCGTGTATTACTGTACCACAAGCTGGAAC
TACAGGTACTACTTTGACTACTGGGGCCAGGGAACCCTGGTCACCGTCTCCTC
AGGGAGTGCATCCGCCCCAACCCTTTTCCCCCTCGTCTCCTGTGAGAATTCC
3'

1A2 Light Chain (SEQ ID NO: 6)

5'GACATTGAGCTCACGCAGTCTCCAGACTTTCAGTCTGTGACTCCAAAGGA
GAAAGTCACCATCACCTGCCGGGCCAGTCAGAGCATTGGTAGTAGCTTACAC
TGGTACCAGCAGAAACCAGATCAGTCTCCAAAGCTCCTCATCAAGTATGCTT
CCCAGTCCTTCTCAGGGGTCCCCTCGAGGTTCAGTGGCAGTGGATCTGGGAC
AGATTTCACCCTCACCATCAATAGCCTGGAAGCTGAAGATGCTGCAACGTAT
TACTGTCATCAGAGTAGTAGTTTACCTCGGACGTTCGGCCAAGGGACCAAGG
TGGAAATCAAACGAACTGTGGCTGCACCATCTGTCTTCATCTTCCCGCCATCT
GATGAGCAGTTGAAATCTGGAACTGCCTCTGTTGTGCCTGCTGAATAACTT
CTATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTAC
AGCCTCAGCAGCACCCTGACGCTGAGCAAAGCAGACTACGAGAAACACAAA
GTCTACGCCTGCGAAGTCACCCATCAGGGCCTGAGCTCGCCC**GTCACAAAGA
GCTTCAACAGG**3'

FIG. 6B

A7 Heavy Chain (SEQ ID NO: 7)

5'GAGTTTGGGCTGAGCTGGATTTTCCTTGCTGCTATTTTAAAAGGTGTCCAG
TGTGAGGTGCAGCTGGTGGAGTCTGGGGGAGGCTTGGTAAAGCCTGGGGGGT
CCCTTAGACTCTCCTGTGCAGCCTCTGGATTCACTTTCAGTAACGCCTGGATG
AGCTGGGTCCGCCAGGCTCCAGGGAAGGGGCTGGAGTGGGTTGGCCGTATTA
AAAGCAAAACTGATGGTGGGACAACAGACTACGCTGCACCCGTGAAAGGCA
GATTCACCATCTCAAGAGATGATTCAAAAAACACGCTGTATCTGCAAATGAA
CAGCCTGAAAACCGAGGACACAGCCGTGTATTACTGTACGAAACATAGTGGG
AGCTACTACGGATACTTCCAGCACTGGGGCCAGGGCACCCTGGTCACCGTCT
CCTCAGGGAGTGCATCCGCCCCAACCCTTTTCCCCCTCGTCTCCTGTGAGAA
TTCC3'

7 Light Chain (SEQ ID NO: 8)

5'GATATTGAGCTCACTCAGTCTCCACTCTCCCTGCCCGTCACCCCTGGAGA
GCCGGCCTCCATCTCCTGCAGGTCTAGTCAGAGCCTCCTGCATAGTAATGGAT
ACAACTATTTGGATTGGTACCTGCAGAAGCCAGGGCAGTCTCCACAGCTCCT
GATCTATTTGGGTTCTAATCGGGCCTCCGGGGTCCCTGACAGGTTCAGTGGCA
GTGGATCAGGCACAGATTTTACACTGAAAATCAGCAGAGTGGAGGCTGAGGA
TGTTGGGGTTTATTACTGCATGCAAGCTCTACAAACTCCTCGGACGTTCGGCC
AAGGGACCAAGGTGGAAATCAAACGAACTGTGGCTGCACCATCTGTCTTCAT
CTTCCCGCCATCTGATGAGCAGTTGAAATCTGGAACTGCCTCTGTTGTGTGCC
TGCTGAATAACTTCTATCCCAGAGAGGCCAAAGTACAGTGGAANGTGGATAA
CGCCCTCCAATCGGGTAACTCCCANGAGAGTGTCACAGAGCANGACAGCAA
AGACAGCACCTACAGCCTCAGCAGCACCCTGACGCTGAGCAAAGCAGACTAC
GAGAAACACAAAGTCTACGCCTGCGAAGTCACCCATCAAGGCCTGAGCTCGC
CCGTCACAAAGAGCTTCAACAGGA3'

FIG. 6C

SEQUENCE LISTING

<160> NUMBER OF SEQ ID NOS: 21

<210> SEQ ID NO 1
<211> LENGTH: 462
<212> TYPE: DNA
<213> ORGANISM: Homo sapiens

<400> SEQUENCE: 1

| | | | | | | |
|---|---|---|---|---|---|---|
| gagtttgggc | tgagctggct | ttttcttgtg | gctattttaa | aaggtgtcca | gtgtgaggtg | 60 |
| cagctgttgg | agtctggggg | aggcttggta | cagcctgggg | ggtccctgag | actctcctgt | 120 |
| gcagcctctg | gattcacctt | tagcagctat | gccatgagct | gggtccgcca | ggctccaggg | 180 |
| aaggggctgg | agtgggtctc | agctattagt | ggtagtggtg | gtagcacata | ctacgcagac | 240 |
| tccgtgaagg | gccggttcac | catctccaga | gacaattcca | agaacacgct | gtatctgcaa | 300 |
| atgaacagcc | tgagagccga | ggacacggcc | gtatattact | gtgcgaaagc | ccctcctaac | 360 |
| tggggatcgt | ttgactactg | gggccaggga | accctggtca | ccgtctcctc | agggagtgca | 420 |
| tccgccccaa | ccctttcccc | cctcgtctcc | tgtgagaatt | cc | | 462 |

<210> SEQ ID NO 2
<211> LENGTH: 648
<212> TYPE: DNA
<213> ORGANISM: Homo sapiens

<400> SEQUENCE: 2

| | | | | | | |
|---|---|---|---|---|---|---|
| gatattgagc | tcacgcagtc | tccactctcc | ctgcccgtca | cccttggaca | gccggcctcc | 60 |
| atctcctgca | ggtctagtca | aagcctcgta | tacagtgatg | gaaacaccta | cttgaattgg | 120 |
| tttcagcaga | ggccaggcca | atctccaagg | cgcctaattt | ataaggtttc | taactgggac | 180 |
| tctggggtcc | cagacagatt | cagcggcagt | gggtcaggca | ctgatttcac | actgaaaatc | 240 |
| agcagggtgg | aggctgagga | tgttggggtt | tattactgca | tgcaaggtac | acactggcct | 300 |
| cggacgttcg | gccaagggac | caaggtggaa | atcaaacgaa | ctgtggctgc | accatctgtc | 360 |
| ttcatcttcc | cgccatctga | tgagcagttg | aaatctggaa | ctgcctctgt | tgtgtgcctg | 420 |
| ctgaataact | tctatcccag | agaggccaaa | gtacagtgga | aggtggataa | cgccctccaa | 480 |
| tcgggtaact | cccaggagag | tgtcacagag | caggacagca | aggacagcac | ctacagcctc | 540 |
| agcagcaccc | tgacgctgag | caaagcagac | tacgagaaac | acaaagtcta | cgcctgcgaa | 600 |
| gtcacccatc | agggcctgag | ctcgcccgtc | acaaagagct | tcaacagg | | 648 |

<210> SEQ ID NO 3
<211> LENGTH: 474
<212> TYPE: DNA
<213> ORGANISM: Homo sapiens

<400> SEQUENCE: 3

| | | | | | | |
|---|---|---|---|---|---|---|
| gagtttgggc | tgagctgggt | tttcctcgtt | gctcttttaa | gaggtgtcca | gtgtcaggtg | 60 |
| caactggtgg | agtctggggg | aggcgtggtc | cagcctggga | ggtccctgag | actctcctgt | 120 |
| gcagcgtctg | gattcacctt | cagtagctat | ggcatgcact | gggtccgcca | ggctccaggc | 180 |
| aaggggctgg | agtgggtggc | agttatatgg | tatgatggaa | gtaataaata | ctatgcagac | 240 |
| tccgtgaagg | gccgattcac | catctccaga | gacaattcca | agaacacgct | gtatctgcaa | 300 |
| atgaacagcc | tgagagccga | ggacacggct | gtgtattact | gtgcgagaga | tcggagtggg | 360 |
| ctgaggtact | actactacgg | tatggacgtc | tggggccaag | ggaccacggt | caccgtctcc | 420 |

```
tcagggagtg catccgcccc aaccctttc ccctcgtct cctgtgagaa ttcc          474
```

<210> SEQ ID NO 4
<211> LENGTH: 632
<212> TYPE: DNA
<213> ORGANISM: Homo sapiens

<400> SEQUENCE: 4

```
gacattgagc tacgcagtct ccatcttccg tgtctgcatc tgtaggagac agagtcacca   60
tcacttgtcg ggcgagtcag ggtattagca gctggttagc ctggtatcag cagaaaccag  120
ggaaagcccc taagctcctg atctatgttg catcccgttt gcaaagtggg gtcccatcaa  180
ggttcagcgg cagtggatct gggacagatt tcactctcac catcagcagc ctgcagcctg  240
aagattttgc aacttactat tgtcaacagg ctaacagttt ccctcggacg ttcggccaag  300
ggaccaaggt ggaaatcaaa cgaactgtgg ctgcaccatc tgtcttcatc ttcccgccat  360
ctgatgagca gttgaaatct ggaactgcct ctgttgtgtg cctgctgaat aacttctatc  420
ccagagaggc caaagtacag tggaaggtgg ataacgccct ccaatcgggt aactcccagg  480
agagtgtcac agagcaggac agcaaggaca gcacctacag cctcagcagc accctgacgc  540
tgagcaaagc agactacgag aaacacaaag tctacgcctg cgaagtcacc catcagggcc  600
tgagctcgcc cgtcacaaag agcttcaaca gg                                632
```

<210> SEQ ID NO 5
<211> LENGTH: 468
<212> TYPE: DNA
<213> ORGANISM: Homo sapiens

<400> SEQUENCE: 5

```
gaatttgggc tgagctggat tttccttgct gctattttaa aaggtgtcca gtgtgaggtg   60
cagctggtgg agtctggggg aggcttggta aagcctgggg ggtcccttag actctcctgt  120
gcagcctctg gattcacttt cagtaacgcc tggatgagct gggtccgcca ggctccaggg  180
aaggggctgg agtgggttgg ccgtattaaa agcaaaactg atggtgggac aacagactac  240
gctgcacccg tgaaaggcag attcaccatc tcaagagatg attcaaaaaa cacgctgtat  300
ctgcaaatga acagcctgaa aaccgaggac acagccgtgt attactgtac acaagctgg  360
aactacaggt actactttga ctactgggc cagggaaccc tggtcaccgt ctcctcaggg   420
agtgcatccg ccccaaccct ttccccctc gtctcctgtg agaattcc                 468
```

<210> SEQ ID NO 6
<211> LENGTH: 633
<212> TYPE: DNA
<213> ORGANISM: Homo sapiens

<400> SEQUENCE: 6

```
gacattgagc tcacgcagtc tccagacttt cagtctgtga ctccaaagga gaaagtcacc   60
atcacctgcc gggccagtca gagcattggt agtagcttac actggtacca gcagaaacca  120
gatcagtctc caaagctcct catcaagtat gcttcccagt ccttctcagg ggtcccctcg  180
aggttcagtg gcagtggatc tgggacagat ttcacccctca ccatcaatag cctggaagct  240
gaagatgctg caacgtatta ctgtcatcag agtagtagtt acctcggac gttcggccaa  300
gggaccaagg tggaaatcaa acgaactgtg gctgcaccat ctgtcttcat cttcccgcca  360
tctgatgagc agttgaaatc tggaactgcc tctgttgtgt gcctgctgaa taacttctat  420
```

```
cccagagagg ccaaagtaca gtggaaggtg ataacgccc tccaatcggg taactcccag      480
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac agg                                  633
```

<210> SEQ ID NO 7
<211> LENGTH: 471
<212> TYPE: DNA
<213> ORGANISM: Homo sapiens

<400> SEQUENCE: 7

```
gagtttgggc tgagctggat tttccttgct gctattttaa aaggtgtcca gtgtgaggtg       60
cagctggtgg agtctggggg aggcttggta aagcctgggg ggtcccttag actctcctgt      120
gcagcctctg gattcacttt cagtaacgcc tggatgagct gggtccgcca ggctccaggg      180
aaggggctgg agtgggttgg ccgtattaaa agcaaaactg atggtgggac aacagactac      240
gctgcacccg tgaaaggcag attcaccatc tcaagagatg attcaaaaaa cacgctgtat      300
ctgcaaatga acagcctgaa aaccgaggac acagccgtgt attactgtac gaaacatagt      360
gggagctact acggatactt ccagcactgg ggccagggca ccctggtcac cgtctcctca      420
gggagtgcat ccgccccaac ccttttcccc ctcgtctcct gtgagaattc c              471
```

<210> SEQ ID NO 8
<211> LENGTH: 649
<212> TYPE: DNA
<213> ORGANISM: Homo sapiens
<220> FEATURE:
<221> NAME/KEY: modified_base
<222> LOCATION: (462)
<223> OTHER INFORMATION: a, t, c, g, other or unknown
<220> FEATURE:
<221> NAME/KEY: modified_base
<222> LOCATION: (495)
<223> OTHER INFORMATION: a, t, c, g, other or unknown
<220> FEATURE:
<221> NAME/KEY: modified_base
<222> LOCATION: (513)
<223> OTHER INFORMATION: a, t, c, g, other or unknown

<400> SEQUENCE: 8

```
gatattgagc tcactcagtc tccactctcc ctgcccgtca cccctggaga gccggcctcc       60
atctcctgca ggtctagtca gagcctcctg catagtaatg gatacaacta tttggattgg      120
tacctgcaga agccagggca gtctccacag ctcctgatct atttgggttc taatcgggcc      180
tccggggtcc ctgacaggtt cagtggcagt ggatcaggca cagattttac actgaaaatc      240
agcagagtgg aggctgagga tgttggggtt tattactgca tgcaagctct acaaactcct      300
cggacgttcg gccaagggac caaggtggaa atcaaacgaa ctgtggctgc accatctgtc      360
ttcatcttcc cgccatctga tgagcagttg aaatctggaa ctgcctctgt tgtgtgcctg      420
ctgaataact tctatcccag agaggccaaa gtacagtgga angtggataa cgccctccaa      480
tcgggtaact cccangagag tgtcacagag cangacagca agacagcac ctacagcctc      540 agcagcaccc tgacgctgag caaagcagac tacgagaaac acaaagtcta cgcctgcgaa      600
gtcacccatc aaggcctgag ctcgcccgtc acaaagagct tcaacagga                 649
```

<210> SEQ ID NO 9
<211> LENGTH: 11
<212> TYPE: PRT
<213> ORGANISM: Homo sapiens

```
<400> SEQUENCE: 9

Lys Ala Pro Pro Asn Trp Gly Ser Phe Asp Tyr
  1               5                  10

<210> SEQ ID NO 10
<211> LENGTH: 12
<212> TYPE: PRT
<213> ORGANISM: Homo sapiens

<400> SEQUENCE: 10

Lys His Ser Gly Ser Tyr Tyr Gly Tyr Phe Gln His
  1               5                  10

<210> SEQ ID NO 11
<211> LENGTH: 11
<212> TYPE: PRT
<213> ORGANISM: Homo sapiens

<400> SEQUENCE: 11

Thr Ser Trp Asn Tyr Arg Tyr Tyr Phe Asp Tyr
  1               5                  10

<210> SEQ ID NO 12
<211> LENGTH: 15
<212> TYPE: PRT
<213> ORGANISM: Homo sapiens

<400> SEQUENCE: 12

Arg Asp Arg Glu Trp Leu Arg Tyr Tyr Tyr Tyr Gly Met Asp Val
  1               5                  10                  15

<210> SEQ ID NO 13
<211> LENGTH: 9
<212> TYPE: PRT
<213> ORGANISM: Homo sapiens

<400> SEQUENCE: 13

Met Gln Gly Thr His Trp Pro Arg Thr
  1               5

<210> SEQ ID NO 14
<211> LENGTH: 7
<212> TYPE: PRT
<213> ORGANISM: Homo sapiens

<400> SEQUENCE: 14

Met Ala Leu Gln Thr Arg Thr
  1               5

<210> SEQ ID NO 15
<211> LENGTH: 7
<212> TYPE: PRT
<213> ORGANISM: Homo sapiens

<400> SEQUENCE: 15

His Ser Ser Ser Leu Arg Thr
  1               5

<210> SEQ ID NO 16
<211> LENGTH: 7
<212> TYPE: PRT
<213> ORGANISM: Homo sapiens

<400> SEQUENCE: 16
```

```
Gln Ala Asn Ser Phe Arg Thr
  1               5
```

<210> SEQ ID NO 17
<211> LENGTH: 7
<212> TYPE: PRT
<213> ORGANISM: Homo sapiens

<400> SEQUENCE: 17

```
Val Ala Ser Arg Leu Gln Ser
  1               5
```

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gagtttgggc tgagctgg                                                18

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggaattctca caggagacga g                                            21

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gahatygagc tcacbcagtc tcca                                         24

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cctgttgaag ctctttgtga c                                            21

HUMAN ANTIPNEUMOCOCCAL ANTIBODIES FROM NON-HUMAN ANIMALS

This application is a continuation of International Application PCT/US02/18363, filed May 16, 2002, which claims benefit from U.S. Provisional Application No. 60/291,492, filed May 16, 2001, the disclosures of which are incorporated herein by reference in their entireties.

TECHNICAL FIELD OF THE INVENTION

The present invention relates to compositions and methods for treating or preventing *Streptococcus pneumoniae* infection and conditions caused by such infection. Specifically, the present invention relates to human antibodies that specifically bind to *S. pneumoniae* capsular polysaccharide (PPS-3) and nucleic acid molecules that encode the antibodies. The invention also relates to isolated heavy and light chain immunoglobulin molecules of the human antibodies to *S. pneumoniae* PPS-3. The invention further relates to nucleic acid molecules that encode such heavy and light chain immunoglobulin molecules. The invention further comprises human antibodies to *S. pneumoniae* PPS-3 that are chimeric, bispecific, derivatized, single chain antibodies or portions of fusion proteins. The invention also relates to methods of detecting or monitoring *S. pneumoniae* infection. The invention further relates to methods for making the antibodies in a non-human animal and expressing the antibodies in cell lines including hybridomas and recombinant host cell systems. The invention also relates to kits and pharmaceutical compositions comprising the antibodies. The invention further relates to methods of treating or preventing *S. pneumoniae* infection and conditions caused by such infection by administering to a patient any of the compositions described herein.

BACKGROUND OF THE INVENTION

*Streptococcus pneumoniae* is an important human pathogen and a major cause of morbidity and mortality in humans. Available pneumococcal vaccines consist of the purified PPS of the most common serotypes of *S. pneumoniae* that cause disease in adults and children. The rationale underlying pneumococcal vaccination is that type-specific antibodies to pneumococcal capsular polysaccharide (PPS) are required for protection.

However, PPS is poorly immunogenic in many individuals who are at the highest risk for the development of invasive pneumococcal disease, such as young children and immunocompromised individuals. The poor immunogenicity of PPS in infants and young children has been partly overcome by PPS-protein conjugate vaccines, but both conjugated and unconjugated pneumococcal vaccines are poorly immunogenic in many adults. Poor pneumococcal vaccine responses are most common in individuals with antibody defects or deficiency, but the mechanism responsible for this phenomenon is unknown. Accordingly, there is an urgent need for human antibodies for passive immunization of such individuals.

Currently, a limited number of human monoclonal antibodies to a limited number of PPS serotypes have been generated by Epstein-Barr virus transformation of lymphocytes from vaccinated recipients. Epstein-Barr virus transformation is difficult and unpredictable.

We provide human antibodies specific for *S. pneumoniae* PPS-3. Specifically, we provide monoclonal antibodies 1F10/7C5, 3H1, 1A2 and A7 which recognize *S. pneumoniae* PPS-3. Monoclonal antibodies 1F10/7C5, 1A2 and A7 effectively protect against *S. pneumoniae* challenge in passive immunizations.

BRIEF SUMMARY OF THE INVENTION

The present invention provides isolated human antibodies that specifically bind to *S. pneumoniae* capsular polysaccharide (PPS-3). The invention further provides methods for making the antibodies in non-human animals and by expression of the antibodies in cell lines including hybridomas and recombinant host cell systems. The invention also provides kits and pharmaceutical compositions comprising the antibodies. Moreover, the invention provides methods of treating or preventing *S. pneumoniae* infection and conditions caused by such infection by administering to a patient pharmaceutical compositions described herein.

BRIEF DESCRIPTION OF THE DRAWINGS

FIG. 6a shows the nucleic acid sequences of the 1F10/7C5 heavy and light chains (SEQ ID NO: 1 and SEQ ID NO: 2, respectively) and the 3H1 heavy chain (SEQ ID NO: 3).

FIG. 6b shows the nucleic acid sequences of the 3H1 light chain (SEQ ID NO: 4) and the 1A2 heavy and light chains (SEQ ID NO: 5 and SEQ ID NO: 6 respectively).

FIG. 6c shows the nucleic acid sequences of the A7 heavy and light chains (SEQ ID NO: 7 and SEQ ID NO: 8, respectively).

DETAILED DESCRIPTION OF THE INVENTION

Figure 1:
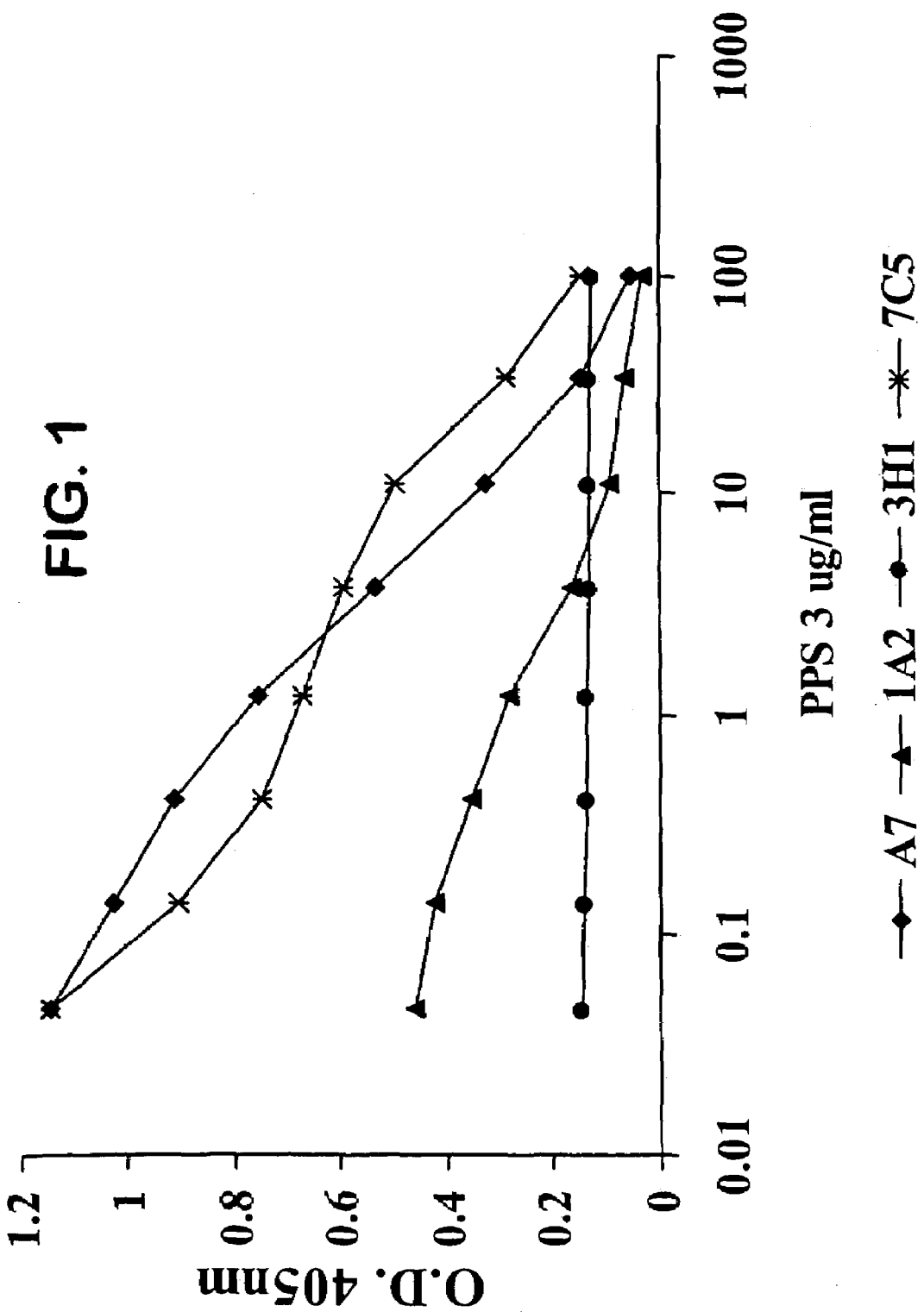
FIG. 1 demonstrates that the Mabs are specific for *S. pneumoniae* PPS-3. The y axis represents the ODs of the Mabs in the presence of the concentration of soluble *S. pneumoniae* PPS-3 indicated on the x axis.

The present invention provides fully human antibodies or antigen-binding portions thereof that specifically bind to *S. pneumoniae* PPS-3. In a preferred embodiment, the fully human antibodies are monoclonal. Other preferred embodiments include nucleic acid molecules comprising nucleotide sequences encoding the all or part of the variable regions of the antibodies' heavy and light chains and amino acid sequences comprising these regions of antibodies' heavy and light chains, and in particular sequences corresponding to heavy and light chain sequences comprising the complementarity determining regions (CDRs). Antibodies having similar binding properties and antibodies (or other antagonists) having similar functionality as antibodies disclosed herein are also provided. Hybridomas expressing such immunoglobulin molecules and monoclonal antibodies are also provided.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The following terms are intended to have the following general meanings as they are used herein:

"B lymphocytic cells or progeny thereof" refer to any cell descending from, or destined for, the B lymphocytic lineage. Examples include, but are not limited to, all B lymphocytes in the B cell developmental pathway starting from the earliest B lymphocyte stem cells through memory B cells, plasma cells, and any hybridomas created in vitro.

"Bispecific antibodies" are single antibodies that have affinities for two separate antigens. For example, a bispecific antibody might recognize *S. pneumoniae* PPS-3 using one combination of heavy and light chains and might recognize a leukocyte cell surface marker using a second combination of heavy and light chains attached to the first combination. See, e.g., McCormick et al., *J. Immunol.* 158:3474–82 (1997).

"Chimeric antibodies" are antibodies that have been altered from their original form to comprise amino acid sequences from another protein. Chimeric antibodies retain at least a portion of the original antibody amino acid sequence, typically the portion comprising the antigen binding region (Fab). Examples of chimeric antibodies include, but are not limited to, bispecific antibodies and fusions with other non-immunoglobulin protein sequences.

"Cytokines" refer generally to signaling molecules of the immune system. Cytokines include, but are not limited to, interleukins (IL), transforming growth factors (TGF), tumor necrosis factors (TNF), lymphotoxins (LT), interferons, granulocyte-macrophage colony stimulating factors (GM-CSF), macrophage CSF, granulocyte CSF, and migration inhibition factors.

"Derivatize" refers to the process of attaching a non-immunoglobulin agent to the immunoglobulin molecules. Examples of derivatizing agents include, but are not limited to, toxins, complement, antibiotics, peptides, polysaccharides, lipids, organic polymers, radiolabels, and inorganic compounds.

"Expression control sequences" refer to sequences that allow for the inducible or constitutive expression of gene sequences under specific conditions or in specific cells. Examples of cellular processes that expression control sequences regulate include, but are not limited to, gene transcription, protein translation, messenger RNA splicing, immunoglobulin isotype switching, protein glycosylation, protein cleavage, protein secretion, intracellular protein localization and extracellular protein homing.

"Fusion proteins" refer to chimeric proteins comprising amino acid sequences of two or more different proteins. Typically, fusion proteins result from in vitro recombinatory techniques well known in the art. However, fusion proteins may result from in vivo crossover or other recombinatory events.

The term "polypeptide fragment" as used herein refers to a polypeptide that has an amino-terminal and/or carboxy-terminal deletion, but where the remaining amino acid sequence is identical to the corresponding positions in the naturally-occurring sequence. Fragments typically are at least 5, 6, 8 or 10 amino acids long, preferably at least 14 amino acids long, more preferably at least 20 amino acids long, usually at least 50 amino acids long, and even more preferably at least 70 amino acids long.

Fragments or analogs of antibodies or immunoglobulin molecules can be readily prepared by those of ordinary skill in the art following the teachings of this specification. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. (Bowie et al., *Science* 253:164 (1991).)

Preferred amino acid substitutions are those which: (1) reduce susceptibility to proteolysis, (2) reduce susceptibility to oxidation, (3) alter binding affinity for forming protein complexes, and (4) confer or modify other physicochemical or functional properties of such analogs. Analogs can include various muteins of a sequence other than the naturally occurring peptide sequence. For example, single or multiple amino acid substitutions (preferably conservative amino acid substitutions) may be made in the naturally occurring sequence (preferably in the portion of the polypeptide outside the domain(s) forming intermolecular contacts). A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al., Nature 354:105 (1991), which are each incorporated herein by reference.

As used herein, the twenty conventional amino acids and their abbreviations follow conventional usage. See Immunology—A Synthesis (2nd Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ϵ-N,N,N-trimethyllysine, ϵ-N-acetyllysine, O-phosphoserine, N-acetylserine, N-formylmethionine, 3-methylhistidine, 5-hydroxylysine, s-N-methylarginine, and other similar amino acids and imino acids (e.g., 4-hydroxyproline). In the polypeptide notation used herein, the lefthand direction is the amino terminal direction and the right-hand direction is the carboxy-terminal direction, in accordance with standard usage and convention.

"Human immunoglobulin molecules" refer to immunoglobulin proteins that are encoded by human immunoglobulin gene sequences.

"Human monoclonal antibodies" refer to antibodies that are members of a population of human antibodies with identical specificities. The population of human antibodies may be produced in a hybridoma or other immortalized cell line as well as in recombinant cell lines expressing the exogenous human antibody gene sequences.

"Immunocompromised patients" refer to patients whose immune responses to foreign antigens or agents is impaired, e.g., by disease (e.g. AIDS), by invasive surgery, or by drug therapies in connection with treatments for other conditions (e.g. organ transplant patients).

"Label" refers to any molecule that attaches to the claimed immunoglobulin a functional characteristic not normally associated with that immunoglobulin. Labels can be attached via chemical modification of the immunoglobulin, recognition of the label by one of the two Fab regions of a bispecific immunoglobulin, affinity for a third agent (e.g. the avidin/biotin interaction), radiolabeling, or as a fusion protein expressed recombinantly. Labels can function as molecular or radioactive tags for clinical or research purposes or as agents for combating S. pneumoniae infection (e.g. toxins or complement proteins). Other examples of labels can include enzymes, fluorescent molecules, magnetic labels, epitope tags (e.g. H. influenza hemaglutinin), antibiotics, complement proteins, and cytokines.

"Surgical patients" refer to any patient subjected to an invasive surgical procedure, typically involving puncturing or incising the dermis.

"Toxins" refer to protein or non-protein compounds that can be attached to antibodies for the purpose of killing the cells to which the antibodies have attached. Examples of toxins include, but are not limited to, complement, antibiotics, peptides, polysaccharides, lipids, organic polymers, radiolabels, and inorganic compounds.

"Vectors" refer to nucleic acid molecules that allow nucleic acid sequences of interest to be cloned, propagated, recombined, mutated, or expressed outside of their native cells. Often vectors have sequences that allow for controlling expression of gene sequences under specific conditions or in specific cells.

To express the antibodies, or antibody portions of the invention, DNAs encoding partial or full-length light and heavy chains, obtained as described above, are inserted into expression vectors such that the genes are operatively linked to transcriptional and translational control sequences. Expression vectors include plasmids, retroviruses, cosmids, YACs, EBV-derived episomes, and the like. The antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors. In a preferred embodiment, both genes are inserted into the same expression vector. The antibody genes are inserted into the expression vector by standard methods (e.g., ligation of complementary restriction sites on the antibody gene fragment and vector, or blunt end ligation if no restriction sites are present).

A convenient vector is one that encodes a functionally complete human $C_H$ or $C_L$ immunoglobulin sequence, with appropriate restriction sites engineered so that any $V_H$ or $V_L$ sequence can easily be inserted and expressed, as described above. In such vectors, splicing usually occurs between the splice donor site in the inserted J region and the splice acceptor site preceding the human C domain, and also at the splice regions that occur within the human $C_H$ exons. Polyadenylation and transcription termination occur at native chromosomal sites downstream of the coding regions. The recombinant expression vector also can encode a signal peptide that facilitates secretion of the antibody chain from a host cell. The antibody chain gene may be cloned into the vector such that the signal peptide is linked in-frame to the amino terminus of the immunoglobulin chain. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification), the neo gene (for G418 selection), and the glutamate synthetase gene.

Nucleic acid molecules encoding anti-PPS-3 antibodies and vectors comprising these nucleic acid molecules can be used for transfection of a suitable mammalian host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors. Methods of transforming cells are well known in the art. See, e.g., U.S. Pat. Nos. 4,399,216, 4,912,040, 4,740,461, and 4,959,455 (which patents are hereby incorporated herein by reference).

Mammalian cell lines available as hosts for expression are well known in the art and include many immortalized cell lines available from the American Type Culture Collection (ATCC). These include, inter alia, Chinese hamster ovary (CHO) cells, NS0, SP2 cells, HeLa cells, baby hamster kidney (BHK) cells, monkey kidney cells (COS), human hepatocellular carcinoma cells (e.g., Hep G2), A549 cells, and a number of other cell lines. Cell lines of particular preference are selected through determining which cell lines have high expression levels. Other cell lines that may be used are insect cell lines, such as Sf9 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Further, expression of antibodies of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

"Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

"XenoMouse™" refers to mice bearing homologously targeted endogenous immunoglobulin loci, rendering them incapable of expressing endogenous murine immunoglobulin, but bearing substantial portions of human immunoglobulin loci. Mice of the XenoMouse™ line are capable of somatic rearrangement of the human immunoglobulin genes, hypermutation of the human immunoglobulin variable regions, and immunoglobulin isotype switching. Therefore, the mice of the XenoMouse™ line are capable of mounting effective humoral responses to antigenic challenge utilizing the human immunoglobulin gene sequences. The resulting antibodies are fully human and can be isolated from the animals themselves, from cultured cells extracted from the animals, or from hybridomas created from XenoMouse™ B lymphocytic lines or progeny thereof. Moreover, the rearranged human gene sequences encoding immunoglobulins raised against specific antigenic challenges can be isolated by recombinant means well known in the art.

Antibody Structure. The basic antibody structural unit comprises a tetramer. Each tetramer is composed of two pairs of polypeptide chains, each pair having one "light" (about 25 kDa) and one "heavy" chain (about 50–70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See, generally, *Immunology*, Ch. 4 (Roitt, I., et al., eds., 6th ed., Harcourt Publishers Ltd., London (2001)) (incorporated by reference in its entirety for all purposes). The variable regions of each light/heavy chain pair form the antibody binding site. Thus, an intact IgG antibody has two binding sites. Except in bifunctional or bispecific antibodies, the two binding sites are the same.

The chains all exhibit the same general structure of relatively conserved framework regions (FR) joined by three hyper variable regions, also called CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of the Kabat Database of Sequences of Proteins of Immunological Interest (Johnson & Wu, *Nucl. Acids Res.* 29:205–06 (2001); or Chothia & Lesk, *J. Mol. Biol.* 196:901–17 (1987); Chothia et al. *Nature* 342:878–83 (1989)).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315–21 (1990); Kostelny et al., *J. Immunol.* 148:1547–53 (1992). In addition, bispecific antibodies may be formed as "diabodies" (Holliger et al., *Proc. Natl. Acad. Sci. U.S.A.* 90:6444–48 (1993)); or "Janusins" (Traunecker et al., *EMBO J.* 10:3655–59 (1991) and Traunecker et al., *Intl. J. Cancer Suppl.* 7:51–52 (1992)). Production of bispecific antibodies can be a relatively labor intensive process compared with production of conventional antibodies and yields and degree of purity are generally lower for bispecific antibodies. Bispecific antibodies do not exist in the form of fragments having a single binding site (e.g., Fab, Fab', and Fv).

Human Antibodies from Non-human Animals. Antibodies with murine or rat variable and/or constant regions are less useful than human antibodies for certain therapeutic uses. The presence of such murine or rat derived proteins can lead to the rapid clearance of the antibodies or can lead to the generation of an immune response against the antibody by a patient. To avoid these problems with murine or rat derived antibodies, one can, e.g., develop humanized antibodies or generate fully human antibodies through the introduction of human antibody function into a rodent so that the rodent would produce fully human antibodies.

The ability to clone and reconstruct megabase-sized human loci in YACs and to introduce them into the mouse germline provides a powerful approach to elucidating the functional components of very large or crudely mapped loci as well as generating useful models of human disease. Furthermore, the utilization of such technology for substitution of mouse loci with their human equivalents could provide unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B-cell development. Furthermore, such a strategy could provide an ideal source for production of fully human monoclonal antibodies (Mabs)—an important milestone towards fulfilling the promise of antibody therapy in human disease. Fully human antibodies are expected to minimize the immunogenic and allergic responses intrinsic to mouse or mouse-derivatized Mabs and thus to increase the efficacy and safety of the administered antibodies. The use of fully human antibodies can therefore be expected to provide a substantial advantage in the treatment of chronic or recurring human diseases, such as inflammation, autoimmunity, cancer and bacterial infections, which potentially require repeated antibody administrations.

One approach toward this goal was to engineer mouse strains deficient in mouse antibody production with large fragments of the human Ig loci in anticipation that such mice would produce a large repertoire of human antibodies in the absence of mouse antibodies. Large human Ig fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using hybridoma technology, antigen-specific human Mabs with the desired specificity could be readily produced and selected.

This general strategy was demonstrated in connection with the generation of the first XenoMouse™ strains. See Green et al., *Nature Genet.* 7:13–21 (1994). The XenoMouse™ strains were engineered with yeast artificial chromosomes (YACs) containing 245 kb- and 190 kb-sized germ line configuration fragments of the human heavy chain locus and kappa light chain locus, respectively, which contained core variable and constant region sequences. Id. The human Ig containing YACs were compatible with the mouse system for both rearrangement and expression of antibodies and were capable of substituting for the inactivated mouse Ig genes. This was demonstrated by their ability to induce B-cell development, to produce an adult-like human repertoire of fully human antibodies, and to generate antigen-specific human monoclonal antibodies. These results also suggested that introduction of larger portions of the human Ig loci containing greater numbers of V genes, additional regulatory elements, and human Ig constant regions might recapitulate substantially the full repertoire that is characteristic of the human humoral response to infection and immunization.

The work of Green et al. was recently extended to the introduction of greater than approximately 80% of the human antibody repertoire through introduction of megabase sized, germline configuration YAC fragments of the human heavy chain loci and kappa light chain loci, respectively, to produce new XenoMouse™ mice. See Mendez et al., *Nature Genet.* 15:146–56 (1997) and Green & Jakobovits, *J. Exp. Med.* 188:483–95 (1998) the disclosures of which are hereby incorporated by reference.

Such an approach is further discussed and delineated in U.S. Pat. Nos. 5,916,771, 5,939,598, 5,985,615, 5,998,209, 6,075,181, 6,091,001, 6,114,598 and 6,130,364. See also WO 91/10741, published Jul. 25, 1991, WO 94/02602, published Feb. 3, 1994, WO 96/34096 and WO 96/33735, both published Oct. 31, 1996, WO 98/16654, published Apr. 23, 1998, WO 98/24893, published Jun. 11, 1998, WO 98/50433, published Nov. 12, 1998, WO 99/45031, published Sep. 10, 1999, WO 99/53049, published Oct. 21, 1999, WO 00 09560, published Feb. 24, 2000 and WO 00/037504, published Jun. 29, 2000. The disclosures of each of the above-cited patents, applications, and references are hereby incorporated by reference in their entirety.

Antibodies in accordance with the present invention are preferably prepared through the utilization of a transgenic mouse that has a substantial portion of the human antibody producing genome inserted but that is rendered deficient in the production of endogenous, murine antibodies. Such mice, then, are capable of producing human immunoglobulin molecules and antibodies and are deficient in the production of murine immunoglobulin molecules and antibodies. Technologies utilized for achieving the same are disclosed in the above-mentioned patents, applications, and references.

Through use of such technology, fully human monoclonal antibodies to S. pneumoniae PPS-3, or the antigen binding portions thereof, were produced. Essentially, we immunized XenoMouse™ lines of mice with S. pneumoniae PPS-3, recovered spleen and lymph node cells (such as B-cells) from the mice that express S. pneumoniae PPS-3 antibodies, fused such recovered cells with nonsecreting myeloma cells to prepare immortal hybridoma cell lines, and screened hybridoma cell lines to identify those that produce antibodies specific to S. pneumoniae PPS-3.

Antibodies in accordance with the present invention can also be expressed in cell lines other than hybridoma cell lines. Sequences encoding particular antibodies can be used for transformation of a suitable host cell. Transformation can be by any known method for introducing polynucleotides into a host cell, for example, packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference). The transformation procedure used in a given instance depends upon the host to be transformed. For example, methods for introducing heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, NS/O, HeLa cells, baby hamster kidney (BHK) cells, monkey kidney cells (COS), human hepatocellular carcinoma cells (e.g., Hep G2), and a number of other cell lines. Cell lines of particular preference are selected through determining which cell lines have high expression levels and produce antibodies with the desired S. pneumoniae PPS-3 binding properties.

Further, expression of antibodies of the invention (or other moieties therefrom) from production cell lines can be enhanced using a number of known techniques. For example, enhanced expression can be realized by the coamplification expression system utilizing dihydrofolate reductase (DHFR) or the glutamine synthetase gene expression system (the GS system). See, e.g., Kaufman and Sharp, J. Mol. Biol. 159:601–21 (1982); European Patent Nos. 0 216 846, 0 256 055, and 0 323 997; and European Patent Application No. 89303964.4.

Antibodies of the invention can also be produced through the generation of an animal or plant that is transgenic for the immunoglobulin heavy and light chain sequences of interest and production of the antibody in a recoverable form therefrom. In connection with the transgenic production in animals, e.g., antibodies can be produced in, and recovered from, the milk of goats, cows, or other mammals. See, e.g., U.S. Pat. Nos. 5,827,690, 5,756,687, 5,750,172, and 5,741,957.

The invention contemplates an isolated human antibody or antigen-binding portion thereof that specifically binds to S. pneumoniae PPS-3. In a preferred embodiment, the isolated human antibody is a monoclonal antibody.

The invention further contemplates an isolated human antibody that mediates complement activation. In one embodiment, the isolated human antibody mediates complement activation by the classical pathway. In another embodiment, the isolated human antibody mediates complement activation by the alternative pathway.

The invention also contemplates that the isolated human antibody or antigen-binding portion thereof enhances resistance of a subject to S. pneumoniae.

The invention contemplates an isolated human antibody or antigen-binding portion thereof that specifically binds to S. pneumoniae PPS-3, wherein the antibody or antigen-binding portion thereof prevents or reduces the severity of conditions or disorders caused by S. pneumoniae infection.

The isolated human antibody or antigen-binding portion thereof that specifically binds to S. pneumoniae PPS-3 of the invention may be immunoglobulin G (IgG), IgM, IgE, IgA or IgD. In some embodiments, the IgA may be an IgA1 or IgA2 subtype and the IgG may be an IgG1, IgG2, IgG3 or IgG4 subtype.

The invention contemplates an isolated human antibody or antigen-binding portion thereof that specifically binds to S. pneumoniae PPS-3 and is labeled. In a preferred embodiment, the label is a radiolabel, an enzyme label, a fluorescent label, a toxin, a magnetic agent, a second antibody, an affinity label, an epitope tag, an antibiotic, a complement protein or a cytokine.

The invention contemplates an isolated human antibody or antigen-binding portion thereof that specifically binds to S. pneumoniae PPS-3 and comprises a kappa light chain. In a preferred embodiment, the variable (V) region of the kappa light chain is encoded by a human Vκ15/A19, Vκ19/A1, Vκ26/A26 or Vκ5/L5 gene. In another preferred embodiment, the joining (J) region of the kappa light chain is encode by a human Jκ1 gene.

The invention contemplates an isolated human antibody or antigen-binding portion thereof that specifically binds to S. pneumoniae PPS-3 and comprises a kappa light chain comprising a CDR3 amino acid sequence shown in Table 2 (SEQ ID NO: 13; SEQ ID NO: 14; SEQ ID NO: 15; SEQ ID NO: 16). The invention also contemplates an isolated human antibody or antigen-binding portion thereof that specifically binds to S. pneumoniae PPS-3 and comprises a kappa light chain comprising the CDR2 and CDR3 amino acid sequences shown for Mab 3H1 in Table 2 (SEQ ID NO: 17; SEQ ID NO: 16, respectively). The invention further contemplates an isolated human antibody or antigen-binding portion thereof that specifically binds to S. pneumoniae PPS-3 and comprises a kappa light chain comprising an amino acid sequence encoded by a nucleic acid sequence shown in FIGS. 6a–c (SEQ ID NO: 2; SEQ ID NO: 4; SEQ ID NO: 6 or SEQ ID NO: 8). A signal sequence may or may not be present in any of the antibodies of the invention. The invention also contemplates an isolated human antibody or antigen-binding portion thereof that specifically binds to S. pneumoniae PPS-3 and comprises a lambda light chain.

The invention contemplates an isolated human antibody or antigen-binding portion thereof that specifically binds to S. pneumoniae PPS-3, comprising a heavy chain composed of variable (V), diversity (D), and joining (J) regions. In a preferred embodiment, the variable region of the heavy chain is encoded in part by a human $V_H3$ gene. In preferred embodiments the variable region of the heavy chain is encoded by a human $V_H3$ gene selected from the group consisting of DP-38/V3-15, DP-50V3-33 and DP-47/V3-23. In another preferred embodiment, the diversity region of the heavy chain is encoded by a human D gene selected from the group consisting of D1-26, D6-13 and D7-27. In another preferred embodiment, the joining region of the heavy chain is encoded by a human J gene selected from the group consisting of JH1, JH4b and JH6b.

The invention contemplates an isolated human antibody or antigen-binding portion thereof that specifically binds to S. pneumoniae PPS-3 and comprises a CDR3 region from a heavy chain as shown in Table 2 (SEQ ID NO: 9; SEQ ID NO: 10; SEQ ID NO: 11; SEQ ID NO: 12). The invention further contemplates an isolated human antibody or antigen-binding portion thereof that specifically binds to S. pneumoniae PPS-3 and comprises a heavy chain comprising an amino acid sequence encoded by a nucleic acid sequence shown in FIGS. 6a–c (SEQ ID NO: 1; SEQ ID NO: 3; SEQ ID NO: 5; SEQ ID NO: 7).

The invention contemplates an isolated human antibody or antigen-binding portion thereof that specifically binds to S. pneumoniae PPS-3 and comprises an antigen binding domain chosen from the list consisting of an Fab fragment, an F(ab')2 fragment and an Fv fragment.

The invention contemplates an isolated human antibody or antigen-binding portion thereof that specifically binds to S. pneumoniae PPS-3 and the antibody is a single chain antibody.

The invention contemplates an isolated human antibody or antigen-binding portion thereof that specifically binds to S. pneumoniae PPS-3 and the antibody is a chimeric antibody. In a preferred embodiment, the chimeric antibody comprises framework regions and CDR regions from different human antibodies. In a more preferred embodiment, the chimeric antibody is bispecific. In a more preferred embodiment, the chimeric antibody is bispecific for S. pneumoniae PPS-3 and a label selected from the list consisting of a radiolabeled molecule, an enzymatic label, a fluorescent label, a toxin, a magnetic agent, a second antibody, an affinity label, an epitope tag, an antibiotic, a complement protein and a cytokine.

The invention contemplates an isolated human antibody or antigen-binding portion thereof that specifically binds to S. pneumoniae PPS-3 wherein the antibody or portion thereof is derivatized. In a preferred embodiment, the antibody or portion thereof is derivatized with polyethylene glycol, at least one methyl or ethyl group or at least one carbohydrate moiety.

One may use the nucleic acid molecules of the invention to generate antibody derivatives using techniques and methods known to one of ordinary skill in the art.

In another embodiment, the nucleic acid molecules, vectors and host cells may be used to make mutated anti-PPS-3 antibodies. The antibodies may be mutated in the variable domains of the heavy and/or light chains to alter a binding property of the antibody. For example, a mutation may be made in one or more of the CDR regions to increase or decrease the Kd of the antibody for PPS-3, to increase or decrease $K_{off}$, or to alter the binding specificity of the antibody. Techniques in site-directed mutagenesis are well-known in the art. See, e.g., Sambrook et al. and Ausubel et al., supra. In a preferred embodiment, mutations are made at an amino acid residue that is known to be changed compared to germline in a variable region of an anti-PPS-3 antibody. In a more preferred embodiment, one or more mutations are made at an amino acid residue that is known to be changed compared to the germline in a variable region of one of the anti-PPS-3 antibodies of the invention. In another embodiment, the nucleic acid molecules are mutated in one or more of the framework regions. A mutation may be made in a framework region or constant domain to increase the half-life of the anti-PPS-3 antibody. A mutation in a framework region or constant domain may also be made to alter the immunogenicity of the antibody, to provide a site for covalent or non-covalent binding to another molecule, or to alter such properties as complement fixation. Mutations may be made in each of the framework regions, the constant domain and the variable regions in a single mutated antibody. Alternatively, mutations may be made in only one of the framework regions, the variable regions or the constant domain in a single mutated antibody.

In another embodiment, a fusion antibody or immunoadhesin may be made which comprises all or a portion of an anti-PPS-3 antibody linked to another polypeptide. In a preferred embodiment, only the variable regions of the anti-PPS-3 antibody are linked to the polypeptide. In another preferred embodiment, the $V_H$ domain of an anti-PPS-3 antibody is linked to a first polypeptide, while the $V_L$ domain of an anti-PPS-3 antibody is linked to a second polypeptide that associates with the first polypeptide in a manner in which the $V_H$ and $V_L$ domains can interact with one another to form an antibody binding site. In another preferred embodiment, the $V_H$ domain is separated from the $V_L$ domain by a linker such that the $V_H$ and $V_L$ domains can interact with one another (see also Single Chain Antibodies). The $V_H$-linker-$V_L$ antibody is then linked to the polypeptide of interest. The fusion antibody is useful to directing PPS-3. In addition, fusion antibodies can be created in which two (or more) single-chain antibodies are linked to one another. This is useful if one wants to create a divalent or polyvalent antibody on a single polypeptide chain, or if one wants to create a bispecific antibody. In one embodiment, the fusion antibody or immunoadhesin is prepared using one or more CDR regions from an anti-PPS-3 antibody.

The invention contemplates a pharmaceutical composition comprising an isolated human antibody or antigen-binding portion thereof that specifically binds to S. pneumoniae PPS-3 and a pharmaceutically acceptable carrier. The invention further contemplates a kit comprising the antibody or antigen-binding portion thereof, a pharmaceutically acceptable carrier therefor, and a container. In a preferred embodiment, the kit further comprises instructions for use.

The invention contemplates a method for treating or preventing or inhibiting S. pneumoniae infection or lessening the severity of a condition or disorder caused by such infection, comprising the step of administering a pharmaceutical composition comprising an antibody of the invention to a patient at risk of being infected with, or currently infected with, S. pneumoniae.

In a preferred embodiment, the human antibody is obtained from a non-human animal. In a more preferred embodiment, the antibody is a monoclonal antibody. In another preferred embodiment, the pharmaceutical composition is administered via injection, transmucosal, oral, inhalation, ocular, rectal, long acting implantation, liposomes, emulsion, cream, topical or sustained release means. In another preferred embodiment, the antibody is a fusion with a second protein. In a more preferred embodiment the second protein is chosen from the list consisting of a toxic peptide moiety, a complement protein, a radiolabeled protein, a cytokine or an antibiotic protein. In another preferred embodiment, the antibody is labeled with a radiolabel, a toxin, a complement protein, a cytokine or an antibiotic. In another preferred embodiment, the patient is an immunocompromised patient. In another preferred embodiment, the pharmaceutical composition further comprises a toxin, complement protein, radiolabeled protein, cytokine, antibiotic, or any combination thereof.

The invention contemplates an isolated cell that produces a human antibody or antigen-binding portion thereof that specifically binds to S. pneumoniae PPS-3. In a preferred embodiment, the cell is chosen from the list consisting of a bacterial cell, a yeast cell, an insect cell, an amphibian cell and a mammalian cell. In a more preferred embodiment, the mammalian cell is selected from the list consisting of a human cell, a mouse cell, a rat cell, a dog cell, a monkey cell, a goat cell, a pig cell, a bovine cell and a hamster cell. In a more preferred embodiment, the mammalian cell is selected from the list consisting of a HeLa cell, a NIH 3T3 cell, a CHO cell, a BHK cell, a VERO cell, a CV-1 cell, a NS/0 cell and a COS cell. In a more preferred embodiment, the cell line is a hybridoma.

The invention contemplates a method of producing an isolated human antibody or antigen-binding portion thereof that specifically binds to S. pneumoniae PPS-3, comprising: a) culturing a non-human cell capable of producing the antibody under conditions in which the antibody is produced; b) isolating the antibody from the cell culture.

In a preferred embodiment, the method of producing an isolated human antibody or antigen-binding portion thereof that specifically binds to S. pneumoniae PPS-3 utilizes a hybridoma.

The invention contemplates the production of an additional human antibody or antigen-binding portion thereof that specifically binds to S. pneumoniae PPS-3, comprising: a) immunizing a non-human animal comprising a human immunoglobulin locus with a S. pneumoniae antigenic composition; b) allowing the non-human animal to mount a humoral response to the antigenic composition; and c) isolating the human antibody from the non-human animal.

The invention contemplates a nucleic acid molecule isolated from a non-human animal that comprises a nucleotide sequence that encodes a human antibody heavy chain or the portion thereof that specifically binds to S. pneumoniae PPS-3. In a preferred embodiment, the nucleic acid molecule is isolated from a hybridoma that produces the human antibody.

The invention contemplates an isolated nucleic acid molecule, or a fragment thereof, comprising a nucleotide sequence encoding a human antibody heavy chain or antigen-binding portion thereof comprising a nucleotide sequence as indicated in FIGS. 6a–c (SEQ ID: 1, SEQ ID: 3, SEQ ID: 5, SEQ ID: 7), wherein the human antibody specifically binds to S. pneumoniae PPS-3. In a preferred embodiment, the isolated nucleic acid molecule comprises the sequence encoding between one to three of the CDR regions of the human antibody. The invention further contemplates an isolated nucleic acid molecule, or a fragment thereof, comprising a nucleic acid sequence encoding a human antibody heavy chain or antigen-binding portion thereof comprising a CDR3 amino acid sequence as indicated in Table 2 (SEQ ID: 9, SEQ ID: 10, SEQ ID: 11, SEQ ID: 12), wherein the human antibody specifically binds to S. pneumoniae PPS-3.

The invention contemplates a vector comprising a nucleic acid molecule, or fragment thereof, encoding a human antibody heavy chain or antigen-binding portion thereof, wherein the antibody specifically binds to S. pneumoniae. In a preferred embodiment, the vector further comprises expression control sequences operably linked to the nucleic acid.

The invention contemplates an isolated nucleic acid molecule, or a fragment thereof, encoding a human antibody light chain or antigen-binding portion thereof comprising a nucleotide sequence as indicated in FIGS. 6a–c (SEQ ID: 2, SEQ ID: 4, SEQ ID: 6, SEQ ID: 8), wherein the antibody specifically binds to S. pneumoniae PPS-3. In a preferred embodiment, the isolated nucleic acid molecule comprises the sequence encoding between one to three of the CDR regions of the human antibody. The invention further contemplates an isolated nucleic acid molecule, or a fragment thereof, comprising a nucleic acid sequence encoding a human antibody light chain or antigen-binding portion thereof comprising a CDR3 amino acid sequence as indicated in Table 2 (SEQ ID: 13, SEQ ID: 14, SEQ ID: 15, SEQ ID: 16), wherein the human antibody specifically binds to S. pneumoniae PPS-3. The invention contemplates an isolated nucleic acid molecule, or a fragment thereof, comprising a nucleic acid sequence encoding a human antibody light chain or antigen-binding portion thereof comprising CDR2 and CDR3 amino acid sequences as indicated in Table 2 for Mab 3H1 (SEQ ID: 17; SEQ ID: 16), wherein the human antibody specifically binds to S. pneumoniae PPS-3.

The invention contemplates a vector comprising a nucleic acid molecule, or fragment thereof, encoding a human antibody light chain or antigen-binding portion thereof that specifically binds to S. pneumoniae. In a preferred embodiment, the vector further comprises an expression control sequence operably linked to the nucleic acid.

The invention contemplates an isolated host cell comprising: a) a nucleic acid molecule that was isolated from a non-human animal and encodes a light chain or the antigen-binding portion thereof of a human antibody that specifically binds to S. pneumoniae PPS-3; or b) a vector comprising the nucleic acid molecule.

The invention contemplates an isolated host cell comprising: a) a nucleic acid molecule that was isolated from a non-human animal and encodes a heavy chain or the antigen-binding portion thereof of a human antibody that specifically binds to S. pneumoniae PPS-3; or b) a vector comprising the nucleic acid molecule.

The invention contemplates an isolated host cell comprising: a) a nucleic acid molecule that was isolated from a non-human animal and encodes a heavy chain or the antigen-binding portion thereof and an isolated nucleic acid molecule that encodes a light chain or the antigen-binding portion thereof of a human antibody that specifically binds to S. pneumoniae PPS-3; or b) a vector or vectors comprising the nucleic acid molecules.

The invention contemplates a method of recombinantly producing the heavy chain or the antigen-binding portion thereof, the light chain or the antigen-binding portion thereof, or both the light chain and heavy chain or antigen-binding portions thereof, of a human antibody that was identified from a non-human animal and specifically binds to S. pneumoniae PPS-3, comprising the step of cultivating the host cells described above under conditions in which the nucleic acid molecules are expressed.

The invention contemplates an isolated human antibody heavy chain or antigen-binding portion thereof, wherein the antibody specifically binds to S. pneumoniae PPS-3, encoded by any of the nucleic acid molecules encoding the heavy chain described above, or isolated from any of the host cells described above.

The invention contemplates an isolated human antibody light chain or antigen-binding portion thereof, wherein the antibody specifically binds to *S. pneumoniae* PPS-3, encoded by any of the nucleic acid molecules encoding the heavy chain described above, or isolated from any of the host cells described above.

The invention contemplates a non-human transgenic animal comprising any of the nucleic acid molecules described above. In a preferred embodiment, the non-human transgenic animal expresses the nucleic acid molecule or molecules. In a more preferred embodiment, the non-human transgenic animal comprises an isolated nucleic acid molecule that encodes a heavy chain or the antigen-binding portion thereof and an isolated nucleic acid molecule that encodes a light chain or the antigen-binding portion thereof of a human antibody that specifically binds to *S. pneumoniae* PPS-3, and the non-human animal expresses both nucleic acid molecules. In a more preferred embodiment, the non-human animal is selected from the list consisting of a mouse, a rat, a hamster, a cow, a sheep, a primate, a horse and a pig. In a more preferred embodiment, a human antibody resulting from expression of the isolated nucleic acid molecules or portions thereof is expressed on the surface of cells derived from the animal's B lymphocytic cells or progeny thereof. In another preferred embodiment, the human antibody resulting from expression of the isolated nucleic acid molecules or a portion thereof is secreted into the lymph, blood, milk, saliva, or ascites of the animal.

The invention contemplates a fusion protein comprising an isolated human antibody or antigen-binding portion thereof that specifically binds to *S. pneumoniae* PPS-3 and a second polypeptide sequence. In a preferred embodiment, the second polypeptide sequence is chosen from the list consisting of an epitope tag, an affinity tag, a toxic polypeptide, an antibiotic, an enzyme, a second antibody sequence, a complement protein, and a cytokine.

The invention contemplates an isolated human antibody or antigen-binding portion thereof that specifically binds to *S. pneumoniae* PPS-3, wherein the heavy chain isotype of the antibody is mu, gamma, delta, epsilon or alpha.

The invention contemplates an isolated human antibody or antigen-binding portion thereof that specifically binds to *S. pneumoniae* PPS-3, wherein the antibody or antigen-binding portion thereof is produced by a process comprising the steps of:

a) immunizing a non-human animal comprising a human immunoglobulin locus with an antigen selected from the group consisting of an *S. pneumoniae* PPS-3 preparation, a virulent *S. pneumoniae* cell preparation, an attenuated *S. pneumoniae* cell preparation, and a killed *S. pneumoniae* cell preparation; b) allowing the non-human animal to mount an immune response to the antigen; and c) isolating the antibody from the non-human animal.

The invention contemplates an isolated human antibody or antigen-binding portion thereof isolated from an animal or cell that was free of contaminating human biomaterials. In a preferred embodiment, the biomaterials are viruses, enzymes, hormones, cytokines, receptors, receptor ligands, immunoglobulins, complement, nuclear proteins, and cytoplasmic signaling proteins. In a more preferred embodiment, the viruses are Epstein-Barr virus or retroviruses.

Pharmaceutical compositions may be manufactured by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art. For ocular administration, suspensions in an appropriate saline solution are used as is well known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients include fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator, may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, such as sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g., polyvinyl pyrrolidone; and other sugars or polysaccharides may be substituted for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually with a greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days.

Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The isolated human antibody or an antigen-binding portion thereof that specifically binds to *S. pneumoniae* PPS-3 of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

The kits of the present invention comprise instructions for utilizing the compositions of the present invention for inhibition, prevention or treatment of *S. pneumoniae* infections or conditions or disorders caused by such infection. The printed instructions on the kit enable one of skill in the art to utilize the kit for practicing the methods of the present invention.

The following examples are provided by way of illustration only. They are not intended to limit the scope of the invention disclosed herein.

EXAMPLE 1

Generation of Monoclonal Antibodies to
*Strevtococcus pneumoniae* Capsular Polysaccaride
(PPS-3)

We vaccinated transgenic mice comprising human immunoglobulin loci (XenoMouse™; Mendez et al., *Nat. Genet.* 15, pp. 146–56 (1997)) with a *S. pneumoniae* PPS-3 conjugate produced from purified PPS-3 (Strain 10813, ATCC). See, e.g., Russell et al., *Infection Immunity* 68:1820–26 (2000). In this experiment, we used PPS-3-Tetanus toxoid conjugate (PPS-3-TT) and, as a control, we vaccinated XenoMouse™ mice with commercially available TT. We vaccinated the XenoMouse™ mice subcutaneously at the base of the tail with a total dose of 2.5 µg of PPS-3-TT or TT. We isolated splenocytes from the vaccinated XenoMouse™ mice at 7 or 14 days after vaccination and generated hybridomas by fusion of splenocytes with mouse myeloma cell line NSO and propagated the cells using ClonaCell™-HY (Stem Cell Technologies Inc., Vancouver, Canada) according to the manufacturer's instructions.

We then tested the approximately 100 hybridoma cell lines for secretion of Mabs that reacted with PPS-3 as follows. We first adsorbed supernatants from the hybridoma cell lines with purified pneumococcal cell-wall polysaccharide (CWPS; Statens Seruminstitut, Copenhagen, Denmark). We then incubated serial dilutions of the supernatants in polystyrene ELISA plates (Corning Glass Works, Corning, N.Y.) that had been coated with 10 µg/ml PPS-3 (ATCC 6303) and incubated at 37° C. for 1 hour. We washed the plates and incubated at 37° C. for 1 hour with alkaline-phosphatase (AP) conjugated goat anti-human reagents to IgG, IgM, IgA and kappa light chains and a goat anti-mouse reagent specific for lambda light chains (Fisher Biotech, Fisher Scientific, Pittsburgh, Pa.). We then detected antibody binding by developing the plates with p-nitrophenyl phosphate substrate (Sigma, St. Louis, Mo.) and measuring the optical densities at 405 nm with an MRX Microplate Reader (Dynatech Laboratories, Chantilly, Va.). As controls in this experiment, we used a human serum standard from a PPS-vaccinated individual (positive control; Abadi et al., *J. Infect. Dis.* 178:707–16 (1998)) and 30 an IgM myeloma antibody (negative control; Calbiochem, San Francisco, Calif.). We also screened the hybridoma supernatants for binding to staphylococcal protein A (SPA; Sigma), TT, BSA, CWPS and double-stranded DNA (dsDNA) using standard techniques in the art as described in Russell et al., Pirofski et al., *Infect. Immun.* 63: 3005–14 (1995) and *Infect. Immun.* 68:1820–26 (2000).

EXAMPLE 2

Characterization of Mabs to *S. pneumoniae* PPS-3

We designated four of the human Mabs from these hybridomas as 1F10/7C5, 3H11, 1A2 and A7. Each of these Mabs was IgM and reacted with PPS-3 and SPA but did not exhibit significant binding to TT, BSA, CWPS or dsDNA.

We determined whether the antibodies were specific for PPS-3. We performed an ELISA by coating plates with 10 µg/ml PPS-3, adding 5 µg/ml of Mabs 1F10/7C5, 3H11, 1 A2 and A7 and monitoring the ability of increasing concentrations (0.1–100 µg/ml) of soluble PPS-3 to inhibit antibody binding. We also performed the reverse assay where we added a fixed amount of the biotinylated Mab to serial dilutions of unlabeled Mabs and incubated in PPS-3-coated plates. In both cases, we also incubated the plates without inhibitor as a positive control. We detected the binding of biotinylated Mab by adding HRP-labeled steptavidin and developing with perokidase substrate (Kirkegaard & Perry Laboratories). We measured the optical densities at 450 nm with an MRX Microplate Reader.

We observed that Mabs A7, 1F10/7C5 and 1A2 but not 3H1 were inhibited by soluble PPS-3 (see FIG. 1). The concentration of soluble PPS-3 that confers 50% binding to solid phase PPS-3 by Mabs A7, 1A2, 3H1 and 1F10/7C5 are 0.077 fmole, 0.231 fmole, 2.577 fmole and 0.103 fmole, respectively. From these data, we calculated the relative apparent affinity constants ($aK_a$), which are the inverse of the soluble PPS-3 antigen concentration at 50% maximal binding. The $aK_a$ values of the Mabs A7, 1A2 and 1F10/7C5 are $1.72 \times 10^7$ $M^{-1}$, $2.58 \times 10^7$ $M^{-1}$, and $1.55 \times 10^7$ $M^{-1}$, respectively. We could not determine the $aK_a$ of Mab 3H1 because PPS-3 did not inhibit its binding.

EXPERIMENT 3

Epitope Specificity

We perform competitive-binding assays to compare the epitope specificity of the Mabs. We biotinylate one test Mab by determining the molar concentration of the Mab and preparing an 0.1 M solution of EZ-link sulfo-NHS-LC Biotin (Pierce, Rockford, Ill.) with N,N-dimethylformamide (DMF; Aldrich, Milwaukee, Wis.). We then slowly add 1 mg biotin while simultaneously vortexing the solution. We incubate the reaction for 1 hour at room temperature and then dialyze the biotinylated Mab overnight into PBS. We perform ELISA binding curves of each Mab on PPS-3-coated plates to determine the concentration of biotinylated Mab that results in 50% saturation and to confirm that the biotinylated Mab binds PPS-3 similarly to unlabeled Mab.

For competition experiments, we add each of the other Mabs at the concentration that results in 50% saturation to equal volumes of dilutions of the biotinylated test Mab and incubate with PPS-3-coated ELISA plates. We also perform the reverse assay by adding a fixed amount of biotinylated Mab to serial dilutions of unlabeled Mabs and incubating with PPS-3-coated ELISA plates. In both assays we also incubate the plates without an inhibitor to confirm that the Mab binds to the PPS-3-coated plate. We detect binding of the biotinylated Mab using HRP-labeled streptavidin which we then develop with peroxidase substrate (Kirkegaard & Perry Laboratories). We measure optical densities at 405 nm using an MRX Microplate Reader.

Figure 2A:
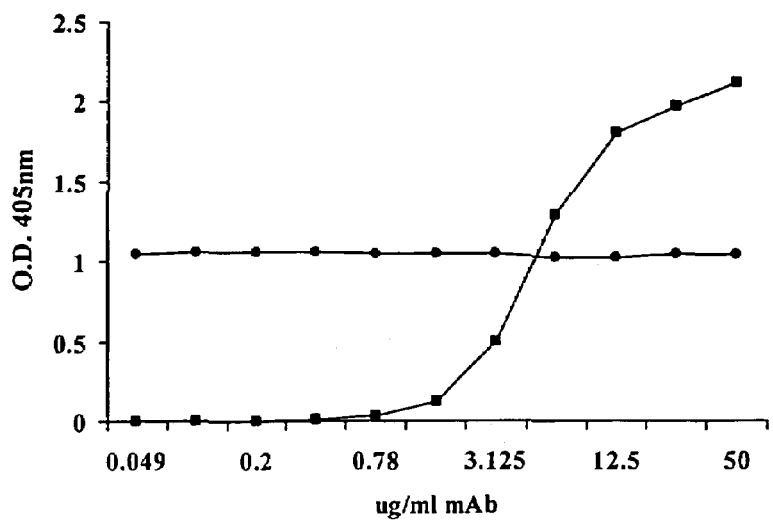
FIG. 2 demonstrates that Mab A7 recognizes a different epitope than Mabs 1A2, 3H1 and 1F10/7C5. The squares represent the signal due to a fixed concentration of unlabeled Mab 1A2 (A), 3H1 (B) or 1F10/7C5 (C) and serial dilutions of biotinylated Mab A7. The circles represent the signal due to a fixed concentration of biotinylated Mab A7 and serial dilutions of the unlabeled Mab 1A2 (A), 3H1 (B) or 1F10/7C5 (C).
Figure 2B:
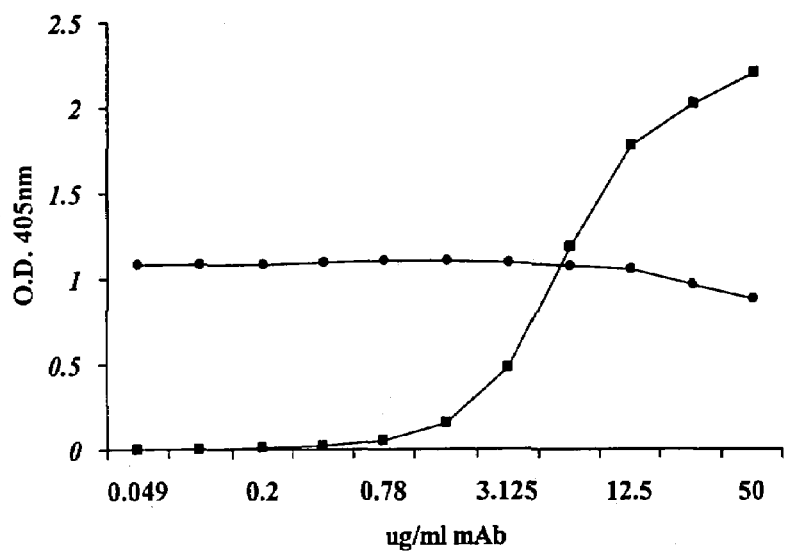
Figure 2C:
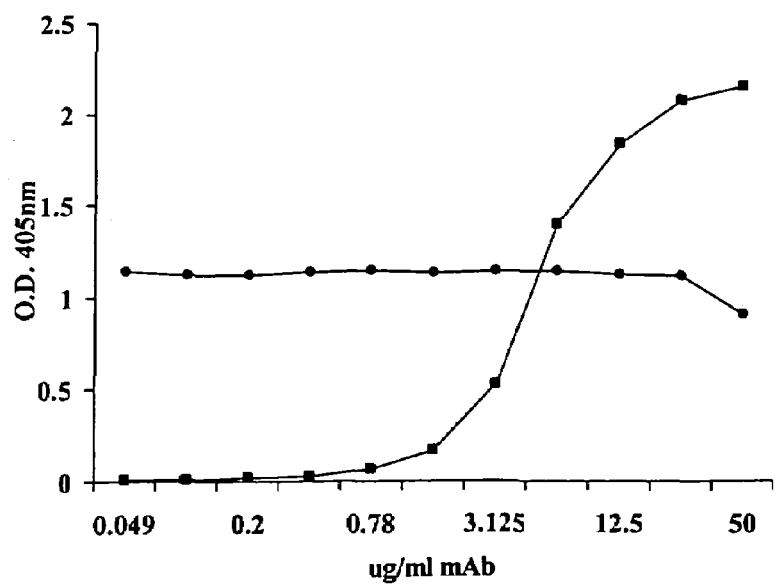
Figure 3A:
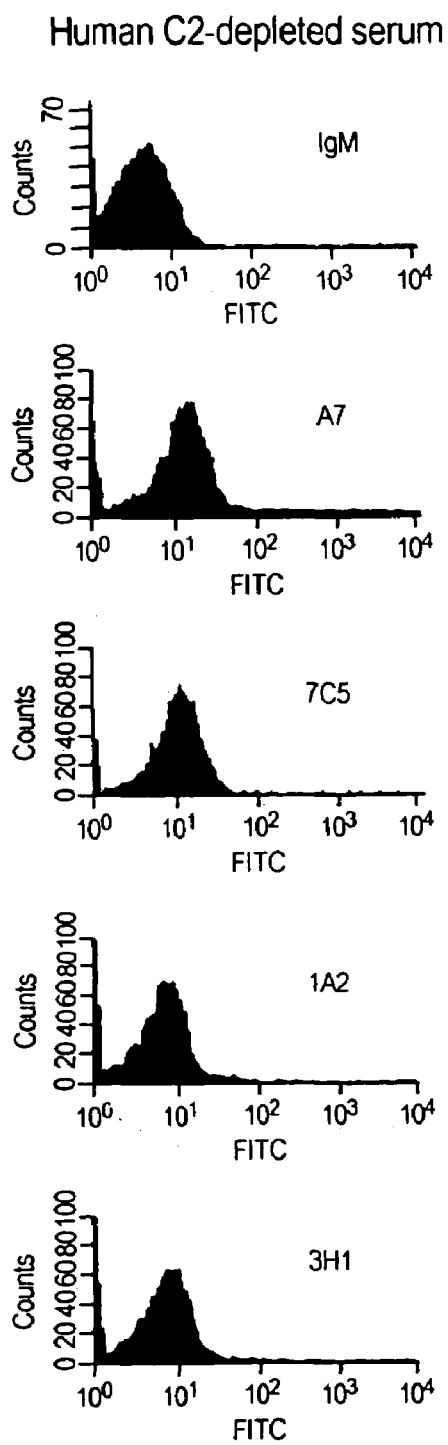
FIG. 3 shows FACS analysis of Mab-mediated deposition of C3 using C2-depleted (A) and Factor B-depleted (B) human serum as complement sources. The geometric mean values for median channel fluorescence intensity in the histograms from top to bottom in panel (A) were 4.1, 11.92, 10.55, 6.6 and 6.34; from top to bottom in panel (B) the geometric mean values for median channel fluorescence intensity in the histograms were 2.53, 9.48, 10.34, 4.46 and 4.58.
Figure 3B:
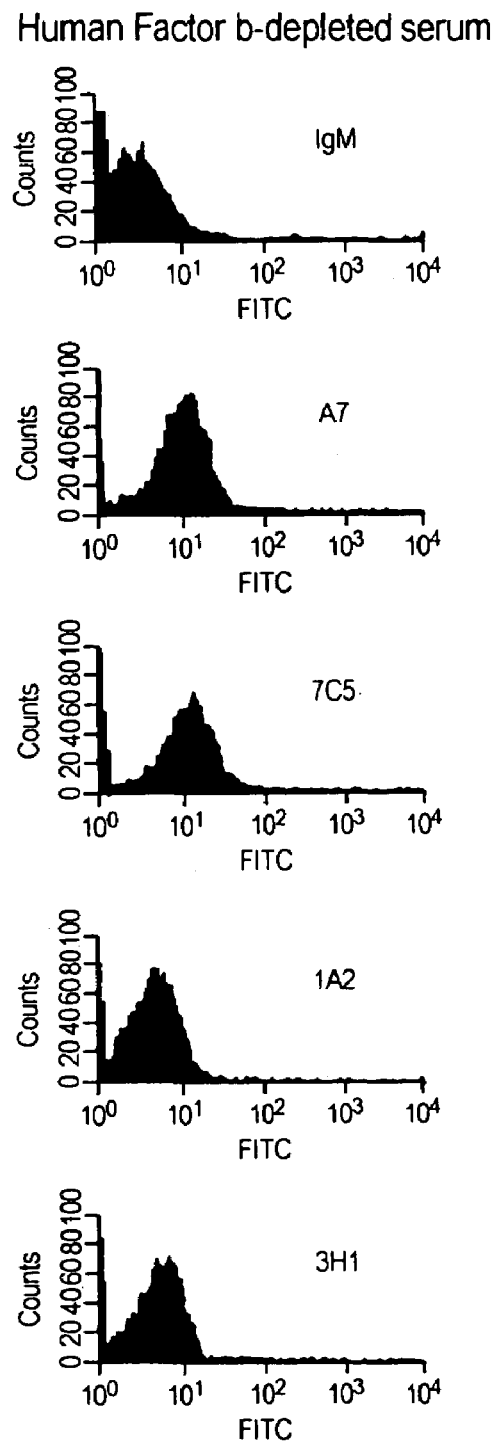

We performed these experiments using biotinylated Mab A7 as the test Mab and demonstrated that A7 have different epitope specificity that 1A2, 3H1 and 1F10/7C5 (FIG. 2). We observed that increasing the concentration of biotinylated Mab A7 without increasing the concentration of the other Mabs results in increased PPS-3 binding which confirmed that the other Mabs do not alter Mab A7 binding. Similarly, when we used a constant concentration of biotinylated Mab A7 and increased the concentration of the other Mabs we observed no change in binding. These experiments indicated that the epitope recognized by A7 is different that the epitope recognized by the other Mabs. However, at very high concentrations of Mab 7C5 (>25 µg/ml) or Mab 3H1 (>12.5 µg/ml) we observed some inhibition of binding by biotinylated Mab A7, suggesting that these Mabs may recognize an epitope that it physically close or overlaps with the epitope recognized by Mab A7. We perform these experiments with each of the other Mabs to compare their epitope specificity.

EXAMPLE 4

Sequence Analysis of Mabs to *S. Pneumoniae* PPS-3

We obtained the nucleic acid molecules encoding the heavy ($V_H$) and light ($V_L$) chains for sequencing using PCR-amplified $V_H$ and $V_L$ cDNA from the hybridomas producing Mabs 1F10/7C5, 3H21, 2A2 and A7. We generated $V_H$ and $V_L$ cDNA by reverse transcription of RNA using $V_H$ and $V_L$ constant region primers. We then amplified the $V_H$ and $V_L$ regions by PCR using $V_H$ and $V_L$ specific primers such as: $V_H$ sense, 5'-GAGTTTGGGCTGAGCTGG-3' (SEQ ID NO: 18); $V_H$ anti-sense, 5'-GGAATTCTCACAG-GAGACGAG-3' (SEQ ID NO: 19); $V_K$ sense, 5'-GA-HATYGAGCTCACBCAGTCTCCA-3' (SEQ ID NO: 20; H represents A, C or T; Y represents C or T and B represents C, G or T); $V_K$ anti-sense, 5'-CCTGTTGAAGCTCTTTGT-GAC-3' (SEQ ID NO: 21). We gel purified and cloned the $V_H$ and $V_K$ PCR products into the pCR1000 plasmid of TA cloning system (Invitrogen™, San Diego, Calif.) according to the manufacturer's instructions. We isolated plasmid DNA using the Maxi plasmid protocol (Qiagen, Inc., Chatsworth, Calif.) and sequenced by dideoxy-chain termination. We compared the variable-region sequences to the database of human immunoglobulin sequences using DNA PLOT (V Base Index; MRC Center for Protein Engineering, Cambridge, United Kingdom; Mukheijee et al., *J. Exp. Med.* 177:1105–16 (1993)). The nucleic acid sequence of PCR products cloned from two independent experiments was determined and they were identical. The sequences of the $V_H$ and $V_L$ regions of these antibodies are shown in FIGS. 6a–c.

We analyzed the nucleic acid sequences and determined which gene segments were used in the Mabs of the invention as shown in Tables 1 and 4. All four Mabs express both human heavy ($V_H$) and light ($V_L$) chain variable region gene transcripts. All of the Mabs use $V_H3$ gene elements: Mabs A7 and 1A2 use the DP-38NV3-15 gene, 1F10/7C5 uses the DP-47/V3-23 gene and 3H1 uses DP-50/V3-33, but their $D_H$ and $J_H$ gene segment usage differs. Mabs A7 and 1A2 express the identical $V_H$, but have different CDR3 regions. Mab 3H1 has a 14 amino acid long CDR3 region whereas the CDR3 region in the other Mabs A7, 7C5 and 1A2 is only 10 or 11 amino acids. The CDR3 regions of the Mabs all manifest one or two somatic mutations as compared with the sequences of their closest germline genes (Table 2). Mabs 1F10/7C5, A7 and 3H1 all have a positively charged residue at position 94, but Mab 1A2 does not. For Mab A7, there was a C to A base change resulting in a change from threonine (T) to lysine (K) in position 94. All four Mabs use a Jκ1 light-chain gene element (A7 uses DPK15, 1A2 uses DPK26, 1F10/7C5 uses DPK19 and 3H1 uses DPK5) and have an arginine (R) at position 96 in the Jκ1 light chain as compared to a tryptophan (W) in the closest germline sequence. Mab 3H1 has two replacement mutations in the Vκ1 CDR2 region as compared to the closest germline gene (Table 2).

EXAMPLE 5

Mabs Mediate Complement Activation

Complement is very important for antibody-mediated protection against *S. pneumoniae* infection. We performed ELISAs to determine if the Mabs could activate the human complement pathways and deposit C3 on PPS-3. We coated ELISA plates with 10 μg/ml PPS-3 with solutions consisting of 10 μg/ml Mab or myeloma IgM (negative control) and 4% of a complement source selected from: C2-deficient, factor B-deficient or normal human serum (Calbiochem, San Diego, Calif.). We then incubated the plates at 37° C. for 1 hour, washed, incubated with goat anti-human C3 (Sigma) at 37° C. for 1 hour and washed again. We detected antibody binding to C3 by incubating the plates with p-nitrophenylphosphate substrate (Sigma). We measured the optical density at 405 nm using an MRX Microplate Reader.

We also monitored C3 deposition by FACS. We incubated heat killed *S. pneumoniae* with 8 mg/ml Mab or the IgM control for 30 min at 37° C. with 1% of each of the complement sources described above. We then washed the samples with HBSS and incubated with FITC-labeled goat anti-human C3 (Cappel, Durham, N.C.) at room temperature for 1 hour. We washed with PBS and resuspended in cold NaCl-EGTA. We analyzed C3 deposition on a FACS and performed flow cytometric analysis on a FACS can (Becton Dickinson Immunological Systems, San Jose, Calif.).

Figure 4:
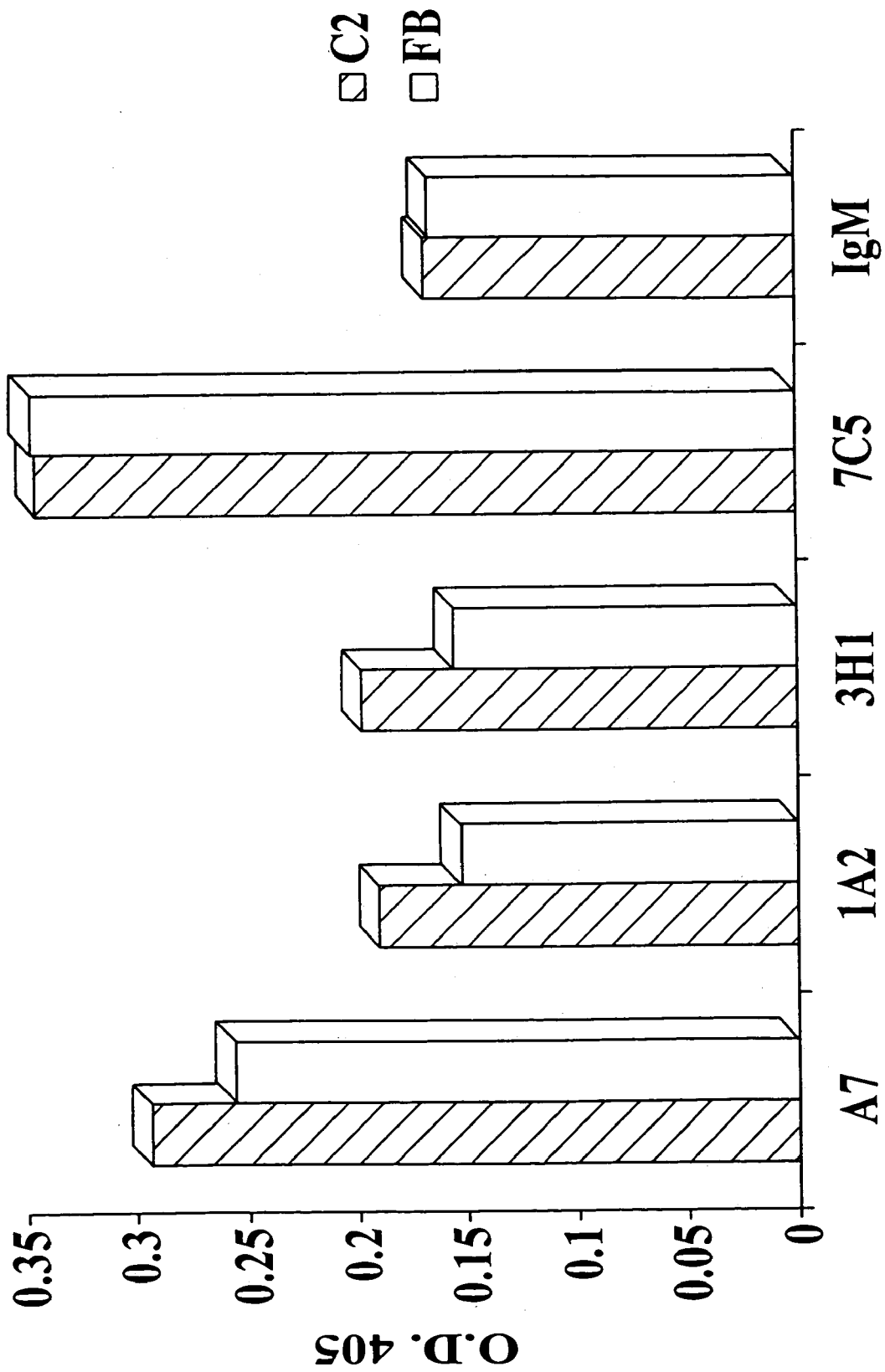
FIG. 4 shows an ELISA determination of Mab-mediated deposition of C3. The light grey bars represent the results using C2-deficient human serum and the dark grey bars represent the results using Factor B-deficient human serum. The y axis represents the OD obtained when the Mabs depicted on the x axis were used.

The influence of the classical complement pathway can be determined from the results using factor-B deficient serum and the influence of the alternative complement pathway from the results using C2-deficient serum. We observed that the Mabs promote deposition of C3 on solid-phase PPS-3 when any of the complement sources were used (FIG. 4). These data indicate that all four Mabs can promote complement binding to PPS-3. We noted that Mabs A7 and 1F10/7C5 mediated greater C3 deposition than either Mabs 1A2 or 3H1 when using either factor B deficient or C2-deficient sera. We confirmed these results in vivo (data not shown).

EXAMPLE 6

Mouse Protection Experiments

We evaluated the protective efficacy of the monoclonal antibodies of the invention. We diluted the Mabs or controls in sterile PBS to concentrations of either 10 μg/ml or 1 μg/ml. We injected 1 ml of the diluted Mabs, or human myeloma IgM (Calbiochem) or only sterile saline as controls, intraperitoneally into several strains of mice. We obtained 6–8 week-old female Balb/c mice from the National Cancer Institute (Bethesda, Md.). We challenged the mice 1 hour after injecting the Mabs by injecting 0.2 ml tryptic soy broth containing 50 colony-forming-units of *Streptococcus pneumoniae* into the lateral tail vein. We confirm the bacterial inoculum by plating. This inoculation dose is 10 times greater than the dose that kills 50% of mice by 48 h after infection ($LD_{50}$ at 48 h). Alternatively, we inoculated mice with *S. pneumoniae* intraperitoneally. We then observe the mice daily and monitor their survival. We compare the number of surviving mice in each group using the Kaplan-Meier log-rank survival test.

Figure 5:
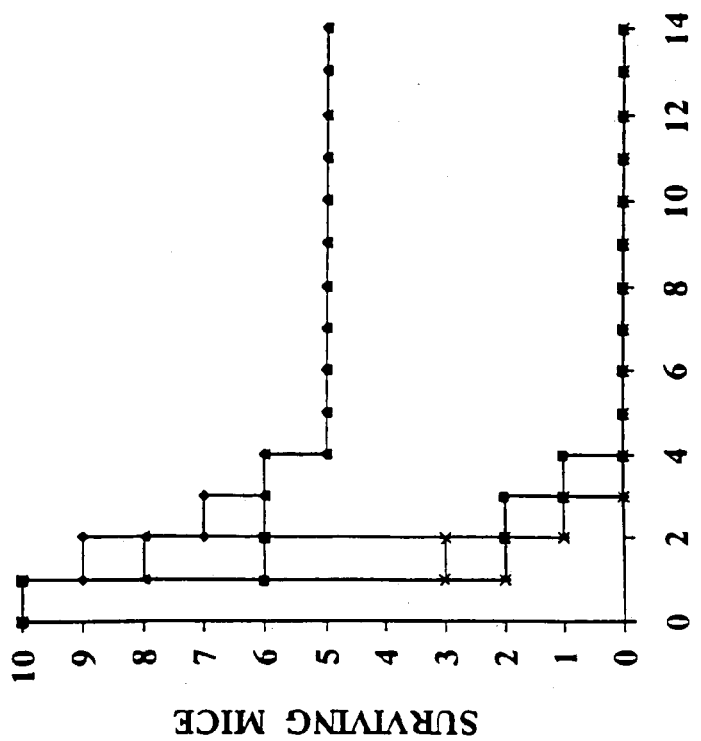
FIG. 5 shows the survival of Balb/c mice after infection with *S. pneumoniae* serotype 3. The left graph shows the results when mice are injected with 10 μg of the indicated Mab, where the y axis indicates the number of mice surviving on the days after infection as indicated on the x axis. The right graph shows the results when mice are injected with 1 μg of the indicated Mab.
Figure 5:
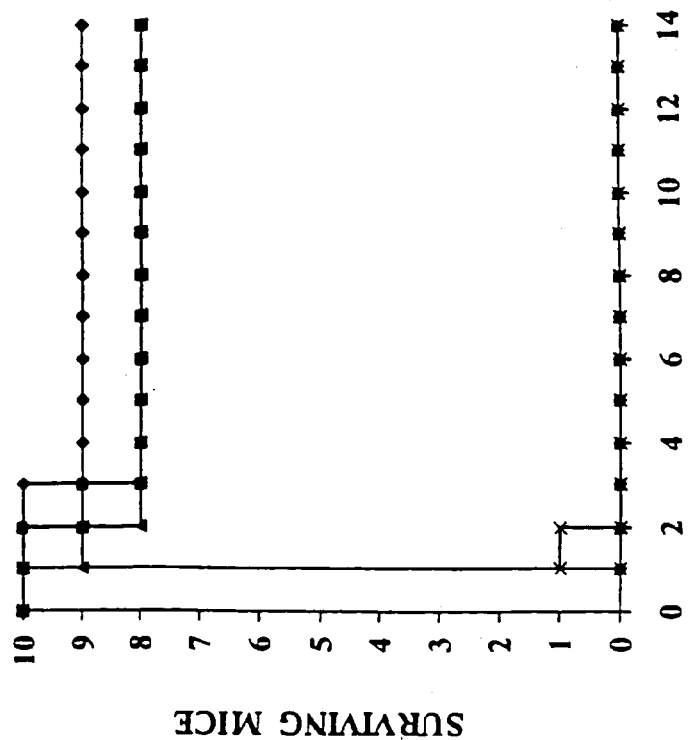

We inoculated groups of mice intraperitoneally with 5, 50 or 500 CFU of *S. pneumoniae* and monitored their survival twice daily. We observed that inoculation of all mouse strains with *S. pneumoniae* resulted in lethal infection within 48 h in mice that had been injected with either negative control (myeloma IgM or PBS; FIG. 5). We determined that the $LD_{50}$ for inoculation with *S. pneumoniae* was ≦5 CFU. In addition, these mice were all noticibly ill within 24 h of infection.

We determined the ability of the Mabs of the invention to protect wild-type mice from *S. pneumoniae* infection. We observed that passive administration of Mabs A7 and 1F10/7C5 prolonged the survival of Balb/c mice infected with *S. pneumoniae* at both 1 μg (50% survival) and 10 μg (80–90% survival) doses of antibody (FIG. 5). Similarly, we observed that passive administration of Mab 1A2 significantly prolonged survival of Balb/c mice infected with *S. pneumoniae*, but only at the 10 μg dose (80–90% survival; FIG. 5). In contrast, when we passively administered either 1 μg or 10 μg of Mab 3H1, we did not observe prolonged survival (FIG. 5).

In all experiments, we confirmed the number of live bacteria in the inoculum by counting colony-forming units (CFU). These experiments demonstrate that human germline genes can be used to produce protective, serotype specific human antibodies to *S. pneumoniae* PPS-3.

Throughout this specification and claims, the word "comprise," or variations such as "comprises" or "comprising" will be understood to imply the inclusion of a stated integer or group of integers but not the exclusion of any other integer or group of integers.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

TABLE 1

The human $V_H$ and $V_L$ gene segments used by IgM Mabs to PPS 3

| $V_H$ (GenBank accession number) | $V_H3$ | $D_H$ | $J_H$ | CDR3 (length in amino acids) |
|---|---|---|---|---|
| 7C5(AF431049) | DP-47/V3-23 | D7-27 | JH4b | 10 |
| A7(AF431055) | DP-38/V3-15 | D1-26 | JH1 | 11 |
| 1A2(AF431053) | DP-38/V3-15 | DG-13 | JH4b | 10 |
| 3H1(AF431051) | DP-50/V3-33 | No match | JH6b | 14 |

| $V_L$ (GenBank accession number) | $V_K l$ | $J_K$ | CDR3 (length in amino acids) |
|---|---|---|---|
| 7C5(AF431050) | DPK19/A1 | JK1 | 9 |
| A7(AF431056) | DPK15/A19 | JK1 | 9 |
| 1A2(AF431054) | DPK26/A26 | JK1 | 9 |
| 3H1(AF431052) | DPK5/L5 | JK1 | 9 |

Table 2

CDR sequences of IgM Mabs to PPS 3

(A)

| | CDR1 | CDR2 | CDR3 | |
|---|---|---|---|---|
| H chain AA code | 1------31 to 35------50 51 52 to 63 | 64 65-----94 | 95 96 97 98 99 100 101 102 103 104 105 106 107 108 | |
| 7C5 | | K A P P N W G S F D Y | (SEQ ID NO: 9) |
| D7-27 | | | | |
| J_H4b | | | | |
| A7 | | | ---------------------Y--------- | (SEQ ID NO: 10) |
| V3-15 | | | | |
| D1-26 | ---T | K H S G S Y Y Y G Y F Q H | |
| J_H1 | | Y--- | | |
| 1A2 | | T S W N Y R Y Y F D Y | (SEQ ID NO: 11) |
| D6-13 | | ------Y | E--------- | |
| J_H4b | | | | |
| 3H1 | | R D R E W L R Y Y Y Y G M D V | (SEQ ID NO: 12) |
| D-no match | | | | |
| J_H6b | | | | |

(B)

| | CDR1 | CDR2 | CDR3 |
|---|---|---|---|
| L chain AA code | 1------24 to 35------50 51 52 53 54 55 56------89 | 90 91 92 93 94 95 96 97 | |
| | | Y--- | |

Table 2-continued

CDR sequences of IgM Mabs to PPS 3

| | | | |
|---|---|---|---|
| 7C5 | | M Q G T H W P R T | (SEQ ID NO: 13) |
| | DPK19 | ---------------- | |
| | J$_\kappa$1 | W--- | |
| A7 | | M - A L Q T - R T | (SEQ ID NO: 14) |
| | DPK15 | ---------------- | |
| | J$_\kappa$1 | W--- | |
| 1A2 | | H - S S S L - R T | (SEQ ID NO: 15) |
| | DPK26 | ---------------- | |
| | J$_\kappa$1 | W--- | |
| 3H1 | | Q - A N S F - R T | (SEQ ID NO: 16) |
| | DPK5 | ---------------- | |
| | J$_\kappa$1 | W--- | |

(SEQ ID NO: 17)
V A S R L Q S---------Q - A N S F - R T
A----------S------------------

---

We claim:

1. A monoclonal antibody or an antigen-binding fragment thereof that specifically binds the capsular polysaccharide of *Streptococcus pneumoniae* serotype 3 (*S. pneumoniae* PPS-3), wherein said antibody or fragment comprises a heavy chain amino acid sequence comprising an amino acid sequence selected from the group consisting of:

(a) the amino acid sequence encoded by the DNA sequence set forth in SEQ ID NO: 1;

(b) the amino acid sequence of residues 31 to 104, inclusive, of the amino acid sequence encoded by the DNA sequence set forth in SEQ ID NO: 1; and (c) the CDR1, CDR2 and CDR3 amino acid sequences encoded by the DNA sequence set forth in SEQ ID NO: 1.

2. The antibody or antigen binding fragment according to claim 1, further comprising a light chain amino acid sequence, said light chain amino acid sequence comprising an amino acid sequence selected from the group consisting of:
  (a) the amino acid sequence encoded by the DNA sequence set forth in SEQ ID NO: 2;
  (b) the amino acid sequence of residues 24 to 97, inclusive, of the amino acid sequence encoded by the DNA sequence set forth in SEQ ID NO: 2; and
  (c) the CDR1, CDR2 and CDR3 amino acid sequences encoded by the DNA sequence set forth in SEQ ID NO: 2.

3. A monoclonal antibody or an antigen-binding fragment thereof that specifically binds the capsular polysaccharide of *Streptococcus pneumoniae* serotype 3 (*S. pneumoniae* PPS-3), wherein said antibody or fragment comprises a heavy chain amino acid sequence comprising an amino acid sequence selected from the group consisting of:
  (a) the amino acid sequence encoded by the DNA sequence set forth in SEQ ID NO: 3;
  (b) the amino acid sequence of residues 31 to 108, inclusive, of the amino acid sequence encoded by the DNA sequence set forth in SEQ ID NO: 3; and
  (c) the CDR1, CDR2 and CDR3 amino acid sequences encoded by the DNA sequence set forth in SEQ ID NO: 3.

4. The antibody or antigen binding fragment according to claim 3, further comprising a light chain amino acid sequence, said light chain amino acid sequence comprising an amino acid sequence selected from the group consisting of:
  (a) the amino acid sequence encoded by the DNA sequence set forth in SEQ ID NO: 4;
  (b) the amino acid sequence of residues 24 to 97, inclusive, of the amino acid sequence encoded by the DNA sequence set forth in SEQ ID NO: 4; and
  (c) the CDR1, CDR2 and CDR3 amino acid sequences encoded by the DNA sequence set forth in SEQ ID NO: 4.

5. A monoclonal antibody or an antigen-binding fragment thereof that specifically binds the capsular polysaccharide of *Streptococcus pneumoniae* serotype 3 (*S. pneumoniae* PPS-3), wherein said antibody or fragment comprises a heavy chain amino acid sequence comprising an amino acid sequence selected from the group consisting of:
  (a) the amino acid sequence encoded by the DNA sequence set forth in SEQ ID NO: 5;
  (b) the amino acid sequence of residues 31 to 104, inclusive, of the amino acid sequence encoded by the DNA sequence set forth in SEQ ID NO: 5; and
  (c) the CDR1, CDR2 and CDR3 amino acid sequences encoded by the DNA sequence set forth in SEQ ID NO: 5.

6. The antibody or antigen binding fragment according to claim 5, further comprising a light chain amino acid sequence, said light chain amino acid sequence comprising an amino acid sequence selected from the group consisting of:
  (a) the amino acid sequence encoded by the DNA sequence set forth in SEQ ID NO: 6;
  (b) the amino acid sequence of residues 24 to 97, inclusive, of the amino acid sequence encoded by the DNA sequence set forth in SEQ ID NO: 6; and
  (c) the CDR1, CDR2 and CDR3 amino acid sequences encoded by the DNA sequence set forth in SEQ ID NO: 6.

7. A monoclonal antibody or an antigen-binding fragment thereof that specifically binds the capsular polysaccharide of *Streptococcus pneumoniae* serotype 3 (*S. pneumoniae* PPS-3), wherein said antibody or fragment comprises a heavy chain amino acid sequence comprising an amino acid sequence selected from the group consisting of:
  (a) the amino acid sequence encoded by the DNA sequence set forth in SEQ ID NO: 7;
  (b) the amino acid sequence of residues 31 to 105, inclusive, of the amino acid sequence encoded by the DNA sequence set forth in SEQ ID NO: 7; and
  (c) the CDR1, CDR2 and CDR3 amino acid sequences encoded by the DNA sequence set forth in SEQ ID NO: 7.

8. The antibody or antigen binding fragment according to claim 7, further comprising a light chain amino acid sequence, said light chain amino acid sequence comprising an amino acid sequence selected from the group consisting of:
  (a) the amino acid sequence encoded by the DNA sequence set forth in SEQ ID NO: 8;
  (b) the amino acid sequence of residues 24 to 97, inclusive, of the amino acid sequence encoded by the DNA sequence set forth in SEQ ID NO: 8; and
  (c) the CDR1, CDR2 and CDR3 amino acid sequences encoded by the DNA sequence set forth in SEQ ID NO: 8.

9. A composition comprising the antibody or antigen-binding fragment thereof according to any one of claims 1, 3, 5 or 7 and a pharmaceutically acceptable carrier.

10. The composition according to claim 9, further comprising a component selected from the group consisting of:
  (a) a diagnostic agent; and
  (b) a therapeutic agent.

11. A method for detecting *S. pneumoniae* serotype-3 infection comprising contacting a sample from a subject suspected of being infected with an antibody or antigen-binding fragment according to any one of claims 1, 5 or 7 and detecting the binding of said antibody or fragment to *S. pneumoniae* serotype 3.

* * * * *